(12) United States Patent
Baum et al.

(10) Patent No.: US 6,869,638 B2
(45) Date of Patent: Mar. 22, 2005

(54) SOURCE REAGENT COMPOSITIONS FOR CVD FORMATION OF GATE DIELECTRIC THIN FILMS USING AMIDE PRECURSORS AND METHOD OF USING SAME

(75) Inventors: Thomas H. Baum, New Fairfield, CT (US); Chongying Xu, New Milford, CT (US); Bryan C. Hendrix, Danbury, CT (US); Jeffrey F. Roeder, Brookfield, CT (US)

(73) Assignee: Advanced Tehnology Materials, Inc., Danbury, CT (US)

( * ) Notice: Subject to any disclaimer, the term of this patent is extended or adjusted under 35 U.S.C. 154(b) by 154 days.

(21) Appl. No.: 09/954,831

(22) Filed: Sep. 18, 2001

(65) Prior Publication Data

US 2002/0187644 A1 Dec. 12, 2002

Related U.S. Application Data

(63) Continuation-in-part of application No. 09/823,196, filed on Mar. 30, 2001.

(51) Int. Cl.$^7$ .......................... B05D 5/12; C23C 16/00; H01L 21/31; C07F 7/28
(52) U.S. Cl. .............................. 427/126.1; 427/255.31; 427/255.32; 438/785; 534/15; 546/2; 556/1; 556/42; 556/51; 556/176
(58) Field of Search ..................... 427/126.1, 255.31, 427/255.32; 438/785; 534/15; 546/2; 556/1, 42, 51, 176

(56) References Cited

U.S. PATENT DOCUMENTS

| | | | |
|---|---|---|---|
| 4,895,709 A | 1/1990 | Laine | 423/344 |
| 5,003,092 A | 3/1991 | Beachley, Jr. | 556/1 |
| 5,139,825 A | 8/1992 | Gordon et al. | 427/255.2 |
| 5,178,911 A | 1/1993 | Gordon et al. | 427/255.2 |
| 5,204,314 A | 4/1993 | Kirlin et al. | 505/1 |
| 5,225,561 A | 7/1993 | Kirlin et al. | 546/256 |
| 5,252,518 A | 10/1993 | Samdhu et al. | 437/200 |
| 5,280,012 A | 1/1994 | Kirlin et al. | 505/1 |
| 5,417,823 A | 5/1995 | Narula et al. | 204/157.4 |
| 5,424,095 A | 6/1995 | Clark et al. | 427/237 |
| 5,453,494 A | 9/1995 | Kirlin et al. | 534/15 |
| 5,536,323 A | 7/1996 | Kirlin et al. | 118/726 |
| 5,583,205 A | 12/1996 | Rees, Jr. | 534/15 |
| 5,593,741 A | 1/1997 | Ikeda | 427/579 |
| 5,726,294 A | 3/1998 | Rees, Jr. | 534/15 |
| 5,820,664 A | 10/1998 | Gardiner et al. | 106/287.17 |
| 5,820,678 A | 10/1998 | Hubert et al. | 118/690 |
| 5,876,503 A | 3/1999 | Roeder et al. | 118/715 |
| 5,919,522 A | 7/1999 | Baum et al. | 427/248.1 |
| 5,924,012 A | 7/1999 | Vaartstra | 438/681 |
| 5,972,430 A | 10/1999 | DiMeo, Jr. | 427/255.32 |
| 5,976,991 A | 11/1999 | Laxman et al. | 438/786 |
| 6,013,553 A | 1/2000 | Wallace et al. | 438/287 |
| 6,015,917 A | 1/2000 | Bhandari et al. | 556/12 |
| 6,020,243 A | 2/2000 | Wallace et al. | 438/287 |
| 6,060,406 A | 5/2000 | Alers et al. | 438/785 |
| 6,110,529 A | 8/2000 | Gardiner et al. | 427/250 |
| 6,159,855 A | 12/2000 | Vaartstra | 438/681 |
| 6,177,135 B1 | 1/2001 | Hintermaier et al. | 427/255.31 |
| 6,348,412 B1 | 2/2002 | Vaartstra | 438/681 |
| 6,399,208 B1 | 6/2002 | Baum et al. | 428/446 |

FOREIGN PATENT DOCUMENTS

| | | | |
|---|---|---|---|
| JP | 06-80413 A | 3/1994 | |
| WO | WO/00/67300 | 11/2000 | H01L/21/00 |

OTHER PUBLICATIONS

Linde et al., Z. anorg. allg. Chem., vol. 409, pp. 199–214 (1974).*

Jones, et al., "MOCVD of Zirconia Thin Films by Direct Liquid Injection Using a New Class of Zirconium Precursor", Chem. Vap. Dep., vol. 4, 1998, pp. 46–49.

D.C. Bradley, et al., "Metalorganic Compounds Containing Metal–Nitrogen Bonds: Part I, Some Dialkyamino Derivatives of Titanium and Zirconium", J. Chem. Soc., 1960, 3857).

(List continued on next page.)

*Primary Examiner*—Porfirio Nazario-Gonzalez
(74) *Attorney, Agent, or Firm*—Margaret Chappuis; Steven Hultquist, Esq.

(57) ABSTRACT

A CVD Method of forming gate dielectric thin films on a substrate using metalloamide compounds of the formula $M(NR^1R^2)_x$, or

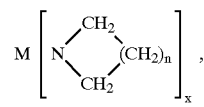

wherein M is Zr, Hf, Y, La, Lanthanide series elements, Ta, Ti, or Al; N is nitrogen; each of $R^1$ and $R^2$ is same or different and is independently selected from H, aryl, perfluoroaryl, $C_1$–$C_8$ alkyl, $C_1$–$C_8$ perfluoroalkyl, alkylsilyl; and x is the oxidation state on metal M; and an aminosilane compound of the formula $H_xSiA_y(NR^1R^2)_{4-x-y}$ or

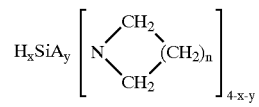

wherein H is hydrogen; x is from 0 to 3; Si is silicon; A is a halogen; Y is from 0 to 3; N is nitrogen; each of $R^1$ and $R^2$ is same or different and is independently selected from the group consisting of H, aryl, perfluoroaryl, $C_1$–$C_8$ alkyl, and $C_1$–$C_8$ perfluoroalkyl; and n is from 1–6. By comparison with the standard $SiO_2$ gate dielectric materials, these gate dielectric materials provide low levels of carbon and halide impurity.

46 Claims, 7 Drawing Sheets

OTHER PUBLICATIONS

D.C. Bradley, et al., "Metalorganic Compounds Containing Metal–Nitrogen Bonds: Part III. Dialkylamino Compounds of Tantalum", Canadian J. Chem., 40, 1355 (1962).

S. Giles, et al., "Deposition of (Ti,Al)N thin films by organometallic chemical vapor deposition: thermodynamic predictions and experimental results", Elsevier Science, SA, Surface and Coatings Technology, 94–95 (1997), pp. 285–290.

Kozoh Sugiyama, et al., "Low Temperature Deposition of Metal Nitrides by Thermal Decomposition of Organometallic Compounds", Journal of the Electrochemical Society, vol. 122, No. 11, Nov. 1975.

R. Juza, et al., "Ammonothermal Synthesis of Magnesium and Beryilium Amides", Angew. Chem. Inte. Ed., 5, (2), 247 (1966).

* cited by examiner

SOURCE REAGENT COMPOSITIONS FOR CVD FORMATION OF GATE DIELECTRIC THIN FILMS USING AMIDE PRECURSORS AND METHOD OF USING SAME

This is a continuation in part of application Ser. No. 09/823,196, filed Mar. 30, 2001.

BACKGROUND OF THE INVENTION

1. Field of the Invention

The present invention relates to chemical vapor deposition processes and source reagent compositions useful for the formation of single component or multicomponent high dielectric constant thin films that may be used in semiconductor materials.

2. Description of the Related Art

Semiconductor devices such as field effect transistors (FET) and metal oxide semiconductor capacitors (MOS-caps) are common in the electronics industry. Such devices may be formed with dimensions that enable thousands or even millions of devices to be formed on a single-crystal substrate and interconnected to perform useful functions in an integrated circuit such as a microprocessor.

The general structure and operation of a field effect transistor is as follows. With reference to FIG. 1, a simplified field effect transistor is shown in cross-section. In a field effect transistor a portion of the substrate (or epi-layer) 100 near the surface is designated as the channel 120 during processing. Channel 120 is electrically connected to source 140 and drain 160, such that when a voltage difference exists between source 140 and drain 160, current will tend to flow through channel 120. The semiconducting characteristics of channel 120 are altered such that its resistivity may be controlled by the voltage applied to gate 200, a conductive layer overlying channel 120. Thus by changing the voltage on gate 200, more or less current can be made to flow through channel 120. Gate 200 and channel 120 are separated by gate dielectric 180; the gate dielectric is insulating, such that between gate 200 and channel 120 the current flow during operation is small compared to the source to drain current (although "tunneling" current is observed with thin dielectrics.) However, the gate dielectric allows the gate voltage to induce an electric field in channel 120, giving rise to the name "field effect transistor." The general structure of a MOS-cap can be visualized as layers 200, 180 and 120 of FIG. 1 without the source and drain. The MOS-cap functions as a capacitor.

$SiO_2$ represents the highest quality gate dielectric material 180 so far developed in silicon technology with low defects and low surface state density. One important advantage of $SiO_2$ is that it may be grown from the silicon substrate at elevated temperatures in an oxidizing environment. It is well known in the art, that thermally grown oxides tend to have fewer defects, (i.e. pinholes), than deposited materials. Thus, $SiO_2$ has persisted as the dielectric material in most silicon device structures.

Generally, integrated circuit performance and density may be enhanced by decreasing the size of the individual semiconductor devices on a chip. Unfortunately, field effect semiconductor devices produce an output signal that is proportional to the length of the channel, such that scaling reduces their output. This effect has generally been compensated for by decreasing the thickness of gate dielectric 180, thus bringing the gate in closer proximity to the channel and enhancing the field effect.

As devices have scaled to smaller and smaller dimensions, the gate dielectric thickness has continued to shrink. Although further scaling of devices is still possible, scaling of the gate dielectric thickness has almost reached its practical limit with the conventional gate dielectric materials: silicon dioxide, silicon oxy-nitride and silicon nitride. Further scaling of silicon dioxide gate dielectric thickness will involve problems such as: extremely thin layers allowing for large leakage currents due to direct tunneling through the oxide. Because such layers are formed literally from a few atomic layers, exact process control is required to repeatably produce such layers. Uniformity of coverage is also critical because device parameters may change dramatically based on the presence or absence of even a single monolayer of dielectric material. Finally, such thin layers form poor diffusion barriers to impurities and dopants.

Consequently, there is a need in the art for alternative dielectric materials, which can be formed in a thicker, layer than silicon dioxide and yet still produce the same field effect performance. This performance is often expressed as "equivalent oxide thickness" (EOT). Although the alternative material layer may be thick, it has the equivalent effect of a much thinner layer of silicon dioxide (commonly called simply "oxide"). In order to have a physically thick layer with a low EOT, the dielectric constant of the insulating material must be increased. Many, if not most, of the attractive alternatives for achieving low equivalent oxide thicknesses are metal oxides, such as tantalum pentoxide, titanium dioxide, barium strontium titanate and other suitable thin films.

However, the formation of such metal oxides as gate dielectrics has been found to be problematic. At typical metal oxide deposition temperatures, the oxygen co-reactant or oxygen-containing precursor tends to oxidize the silicon substrate, producing a lower dielectric constant oxide layer at the interface between the substrate and the higher dielectric constant, gate dielectric material. It could be that the transition metal oxide acts as a catalytic source of activated oxygen, that the precursor molecules increase the oxygen activity or that oxygen from the precursor is incorporated in the growing oxide film. Whatever the cause, the presence of this interfacial oxide layer increases the effective oxide thickness, reducing the effectiveness of the alternative gate dielectric material. The existence of the interfacial oxide layer places a severe constraint on the performance of an alternative dielectric field effect device and therefore, is unacceptable.

The use of metal oxide and metal oxy-nitride thin films comprising Zr, Hf, Y, La, Lanthanide series elements, Ta, Ti and/or Al and silicates of these metal oxides and metal oxy-nitrides are regarded as potential material replacements of the $SiO_2$ gate oxides, (ie., U.S. Pat. Nos. 6,159,855 and 6,013,553). However, to ensure a high integrity interface between the silicon and the gate dielectric film these films must be deposited at relatively low temperatures.

The source reagents and methodology employed to form such gate dielectric thin films are extremely critical for the provision of a gate structure having satisfactory electrical performance characteristics in the product device. Specifically, the source reagents and methodology must permit the gate dielectric thin film to form on a clean silicon surface, without the occurrence of side reactions producing predominantly silicon dioxide ($SiO_2$), locally doped $SiO_2$ and/or other impurities, that lower the dielectric constant and compromise the performance of the product microelectronic device. Further, the absence of carbon contamination is highly desirable.

Impurities that are known to lower the dielectric constant and/or increase leakage include among others, carbon and halides, such as fluorine and chlorine. Carbon incorporation into the dielectric thin film would degrade leakage, dielectric constant, and overall electrical performance of the thin film. In contrast, nitrogen incorporation may exhibit some beneficial properties on the dielectric thin film.

Chemical vapor deposition (CVD) is the thin film deposition method of choice for high-density, large-scale fabrication of microelectronic device structures, and the semiconductor manufacturing industry has extensive expertise in its use. Metalorganic CVD (MOCVD) and more particularly atomic layer MOCVD (ALCVD) are particularly advantageous processes because they allow for lower deposition temperatures and stricter control of the stoichiometry and thickness of the formed layer.

In the formation of gate dielectrics and other semiconductor manufacturing applications it is essential to control the composition of the deposited thin film. The molar ratio(s) of the different elements in the thin film typically corresponds very closely to a predetermined value. Therefore, it is very important to select a precursor delivery system that allows for strict control of the precursors delivered into the CVD chamber. Precursor delivery systems are well known in the art of CVD, (i.e., U.S. Pat. No. 5,820,678, entitled "Solid Source MOCVD System" describes the bubbler delivery approach and U.S. Pat. No. 5,204,314, entitled "Method for Delivering an Involatile Reagent in Vapor Form to a CVD Reactor," and U.S. Pat. No. 5,536,323, entitled "Apparatus for Flash Vaporization Delivery of Reagents," describe the liquid delivery, flash vaporization approach).

The source reagents must be thermally stable to avoid premature decomposition of such source reagents before they reach the CVD reaction chamber during the CVD process. Premature decomposition of source reagents not only results in undesirable accumulation of side products that will clog fluid flow conduits of the CVD apparatus, but also causes undesirable variations in composition of the deposited gate dielectric thin film. Further, particle formation can result in deleterious yields in device fabrication.

Further, Zr, Hf, Y, La, Lanthanide series elements, Ta, Ti, Al and and/or silicon source reagents have to be chemically compatible with other source reagents used in the CVD process. "Chemically compatible" means that the source reagents will not undergo, undesirable side reactions with other co-deposited source reagents, and/or deleterious ligand exchange reactions that may alter the precursor properties, such as transport behavior, incorporation rates and film stoichiometries.

Finally, Zr, Hf, Y, La, Lanthanide series elements, Ta, Ti, Al and/or silicon source reagents selected for MOCVD of dielectric thin films must be able to maintain their chemical identity over time when dissolved or suspended in organic solvents or used in conventional bubblers. Any change in chemical identity of source reagents in the solvent medium is deleterious since it impairs the ability of the CVD process to achieve repeatable delivery and film growth.

There is a continuing need in the art to provide improved Zr, Hf, Y, La, Lanthanide series elements, Ta, Ti, Al and/or silicon source reagents suitable for high efficiency CVD processes, for fabricating corresponding high quality gate dielectric, thin films.

Further, there is a need in the art for oxygen-free Zr, Hf, Y, La, Lanthanide series elements, Ta, Ti, Al and/or silicon source reagents suitable for high efficiency CVD processes, for fabricating corresponding high quality gate dielectric thin films for the reasons as stated hereinabove.

Therefore, it is an object of this invention to provide CVD precursors and CVD processes to deposit high dielectric constant thin films, having minimum carbon and halide incorporation and when deposited on a silicon substrate, minimal $SiO_2$ interlayer.

SUMMARY OF THE INVENTION

The present invention broadly relates to a precursor composition having utility for forming dielectric thin films such as gate dielectric, high dielectric constant metal oxides, and ferroelectric metal oxides and to a low temperature chemical vapor deposition (CVD) process for deposition of such dielectric thin films utilizing such compositions.

As used herein the term "thin film" refers to a material layer having a thickness of less than about 1000 microns.

In one aspect, the present invention relates to a CVD precursor composition for forming a thin film dielectric on a substrate, such precursor composition including at least one source reagent compound selected from the group consisting of:

$$M(NR^1R^2)_x; \text{ and}$$

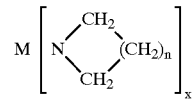

wherein M is selected from the group consisting of: Zr, Hf, Y, La, Lanthanide series elements, Ta, Ti, Al; N is nitrogen; each of $R^1$ and $R^2$ is same or different and is independently selected from the group consisting of H, aryl, perfluoroaryl, $C_1$–$C_8$ alkyl, $C_1$–$C_8$ perfluoroalkyl, alkylsilyl; and x is the oxidation state on metal M; and n is from 1–6.

As used herein, the term "lanthanides series elements" refers to the 14 elements following lanthanum in the Periodic Table, viz., cerium, praseodymium, neodymium, promethium, samarium, europium, gadolinium, terbium, dysprosium, holmium, erbium, thulium, ytterbium and lutetium.

In another aspect, the present invention relates to a CVD precursor composition for forming a thin film dielectric on a substrate, such precursor composition including at least one source reagent compound selected from the group consisting of:

$$H_xSiA_y(NR^1R^2)_{4-x-y} \text{ and}$$

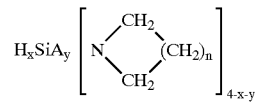

wherein H is hydrogen; x is from 0 to 3; Si is silicon; A is a halogen; Y is from 0 to 3; N is nitrogen; each of $R^1$ and $R^2$ is same or different and is independently selected from the group consisting of H, aryl, perfluoroaryl, $C_1$–$C_8$ alkyl, and $C_1$–$C_8$ perfluoroalkyl; and n is from 1–6.

In a further aspect, the present invention relates to a CVD precursor composition for forming a thin film dielectric on a substrate, such precursor composition including a vapor source reagent selected from the group consisting of:

$$M(NR^1R^2)_x; \text{ and}$$

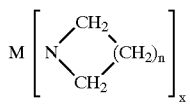

wherein M is selected from the group consisting of: Zr, Hf, Y, La, Lanthanide series elements, Ta, Ti, Al; N is nitrogen; each of $R^1$ and $R^2$ is same or different and is independently selected from the group consisting of H, aryl, perfluoroaryl, $C_1$–$C_8$ alkyl, $C_1$–$C_8$ perfluoroalkyl, alkylsilyl; and x is the oxidation state on metal M; and n is from 1–6.

In a further aspect, the present invention relates to a CVD precursor composition for forming a thin film dielectric on a substrate, such precursor composition including a vapor source reagent mixture including a metalloamide source reagent compound selected from the group consisting of:

$M(NR^1R^2)_x$; and

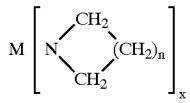

wherein M is selected from the group consisting of: Zr, Hf, Y, La, Lanthanide series elements, Ta, Ti, Al; N is nitrogen; each of $R^1$ and $R^2$ is same or different and is independently selected from the group consisting of H, aryl, perfluoroaryl, $C_1$–$C_8$ alkyl, $C_1$–$C_8$ perfluoroalkyl, alkylsilyl; and x is the oxidation state on metal M; and n is from 1–6; and an aminosilane source reagent compound selected from the group consisting of:

$H_xSiA_y(NR^1R^2)_{4-x-y}$;

and

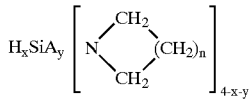

wherein H is hydrogen; x is from 0 to 3; Si is silicon; A is a halogen; Y is from 0 to 3; N is nitrogen; each of $R^1$ and $R^2$ is same or different and is independently selected from the group consisting of H, aryl, perfluoroaryl, $C_1$–$C_8$ alkyl, and $C_1$–$C_8$ perfluoroalkyl; and n is from 1–6.

In a further aspect, the present invention relates to a CVD single source precursor composition for forming a silicate thin film dielectric on a substrate, the precursor composition comprising a vapor source mixture comprising at least one metalloamide vapor source reagent selected from the group consisting of:

$M(NR^1R^2)_x$;

and

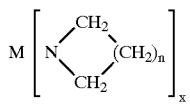

wherein M is selected from the group consisting of: Zr, Hf, Y, La, Lanthanide series elements, Ta, Ti, Al; N is nitrogen; each of $R^1$ and $R^2$ is same or different and is independently selected from the group consisting of H, aryl, perfluoroaryl, $C_1$–$C_8$ alkyl, $C_1$–$C_8$ perfluoroalkyl, alkylsilyl; and x is the oxidation state on metal M; and n is from 1–6; and $H_xSiA_y(NR^1R^2)_{4-x-y}$;

and

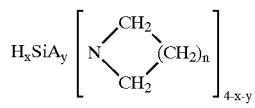

wherein H is hydrogen; x is from 0 to 3; Si is silicon; A is a halogen; Y is from 0 to 3; N is nitrogen; each of $R^1$ and $R^2$ is same or different and is independently selected from the group consisting of H, aryl, perfluoroaryl, $C_1$–$C_8$ alkyl, and $C_1$–$C_8$ perfluoroalkyl; and n is from 1–6.

Another aspect of the present invention relates to a CVD precursor composition comprising a metalloamide source reagent compound and/or an aminosilane source reagent compound as described hereinabove, and a solvent medium in which the source reagent compound(s) is soluble or suspendable.

In another aspect, the invention relates to formation of a dielectric thin film on a substrate from a precursor composition comprising a metalloamide source reagent compound, comprising vaporizing the precursor composition to form a vaporized precursor, and contacting the vaporized precursor with the substrate to deposit a metal-containing film thereon.

In a further aspect, the present invention relates to a CVD method of forming a dielectric thin film on a substrate, comprising the steps of:
vaporizing a precursor composition comprising at least one metalloamide source reagent compound to form a source reagent precursor vapor;
transporting the source reagent precursor vapor into a chemical vapor deposition zone, optionally using a carrier gas;
contacting the source reagent precursor vapor with a substrate in said chemical vapor deposition zone at elevated temperature to deposit a dielectric thin film on the substrate.

In a further aspect, the present invention relates to a CVD method of forming a dielectric thin film on a substrate, comprising the steps of:
vaporizing a multicomponent precursor composition mixture comprising at least one metalloamide source reagent compound and at least one aminosilane source reagent compound, to form a source reagent precursor vapor;
transporting the source reagent precursor vapor into a chemical vapor deposition zone, optionally using a carrier gas;
contacting the source reagent precursor vapor with a substrate in said chemical vapor deposition zone at elevated temperature, to deposit a dielectric thin film on the substrate.

In still a further embodiment, the present invention relates to a method of making a gate dielectric and a gate electrode comprising the steps of:
vaporizing a precursor composition comprising at least one metalloamide source reagent compound to form a source reagent precursor vapor;
transporting the source reagent precursor vapor into a chemical vapor deposition zone, optionally using a carrier gas;

contacting the source reagent precursor vapor with a substrate in said chemical vapor deposition zone at elevated temperature to deposit a dielectric thin film on the substrate;

vaporizing a precursor composition comprising at least one metalloamide source reagent compound to form a source reagent precursor vapor;

transporting the source reagent precursor vapor into a chemical vapor deposition zone, optionally using a carrier gas;

contacting the source reagent precursor vapor with a substrate, comprising the dielectric thin film, in said chemical vapor deposition zone at elevated temperature to deposit a gate conducting thin film on the dielectric thin film.

In yet a further embodiment the present invention relates to a dielectric thin film formed by a method as described hereinabove.

Other aspects, features, and embodiments of the invention will be more fully apparent from the ensuing disclosure and appended claims.

DETAILED DESCRIPTION OF THE INVENTION AND PREFERRED EMBODIMENTS THEREOF

Figure 1:
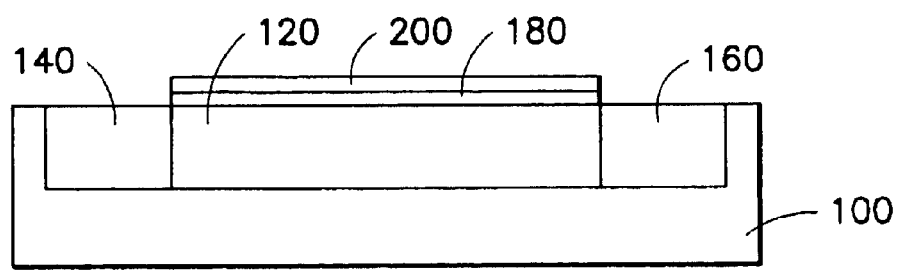
FIG. 1 is a cross-sectional view of a typical prior art integrated circuit field effect transistor.

The disclosure of the following United States patents and patent applications are hereby incorporated by reference in their respective entireties:

U.S. patent application Ser. No. 09/414,133 filed Oct. 7, 1999 in the names of Thomas H. Baum, et al.;

U.S. patent application Ser. No. 09/012,679 filed Jan. 23, 1998 in the names of Gautam Bhandari, et al. and issued Jan. 18, 2000 as U.S. Pat. No. 6,015,917;

U.S. patent application Ser. No. 08/979,465 filed Nov. 26, 1997 in the names of Frank DiMeo, Jr., et al., and issued Oct. 26, 1999 as U.S. Pat. No. 5,972,430;

U.S. patent application Ser. No. 08/835,768 filed Apr. 8, 1997 in the names of Thomas H. Baum, et al., and issued Jul. 6, 1999 as U.S. Pat. No. 5,919,522;

U.S. patent application Ser. No. 08/484,654 filed Jun. 7, 1995 in the names of Robin A. Gardiner et al., and issued Aug. 29, 2000 as U.S. Pat. No. 6,110,529;

U.S. patent application Ser. No. 08/414,504 filed Mar. 31, 1995 in the names of Robin A. Gardiner et al., and issued Oct. 13, 1998 as U.S. Pat. No. 5,820,664;

U.S. patent application Ser. No. 08/280,143 filed Jul. 25, 1994 in the names of Peter S. Kirlin, et al., and issued Jul. 16, 1996 as U.S. Pat. No. 5,536,323;

U.S. patent application Ser. No. 07/927,134, filed Aug. 7, 1992 in the same names;

U.S. patent application Ser. No. 07/807,807 filed Dec. 13, 1991 in the names of Peter S. Kirlin, et al., and issued Apr. 20, 1993 as U.S. Pat. No. 5,204,314;

U.S. patent application Ser. No. 08/181,800 filed Jan. 15, 1994 in the names of Peter S. Kirlin, et al., and issued Sep. 26, 1995 as U.S. Pat. No. 5,453,494;

U.S. patent application Ser. No. 07/918,141 filed Jul. 22, 1992 in the names of Peter S. Kirlin, et al., and issued Jan. 18, 1994 as U.S. Pat. No. 5,280,012;

U.S. application Ser. No. 07/615,303 filed Nov. 19, 1990;

U.S. patent application Ser. No. 07/581,631 filed Sep. 12, 1990 in the names of Peter S. Kirlin, et al., and issued Jul. 6, 1993 as U.S. Pat. No. 5,225,561.

U.S. patent application Ser. No. 07/549,389 filed Jul. 6, 1990 in the names of Peter S. Kirlin, et al.

U.S. patent application Ser. No. 08/758,599 filed Nov. 27, 1996 in the names of Jeffrey F. Roeder, et al., and issued Mar. 2, 1999 as U.S. Pat. No. 5,876,503.

The above-identified applications and patents variously describe source reagent compositions and their synthesis and formulation, as well as CVD techniques including, liquid delivery chemical vapor deposition (LDCVD), and digital or atomic layer chemical vapor deposition (ALCVD) and provide background and assistive information with respect to the practice of the present invention.

The metalloamide precursors of the present invention, when utilized in a CVD process to deposit dielectric thin films on a substrate, result in a dielectric thin film having very low levels of carbon and little or no halide impurity. Further, when the metalloamide precursors of the present invention are used to deposit metal silicate gate dielectric thin films, the thickness of the $SiO_2$ interlayer is minimal or absent and the dielectric constant of the thin film is substantially higher than that of conventional thermal silicon.

Even after a high temperature anneal, the gate dielectric thin films of the invention have low leakage currents, show relatively little growth of interfacial $SiO_2$, and thus have high specific capacitance with low interface state density. The dielectric properties of the thin films produced by the method disclosed herein are substantially improved over conventional silicon gate structures.

As used herein, the term "high temperature" refers to a temperature in excess of 800° C.

The invention in one embodiment relates to a CVD precursor composition for forming a thin film dielectric on a substrate, such precursor composition including a metal loamide source reagent compound selected from the group consisting of:

$M(NR^1R^2)_x$; and

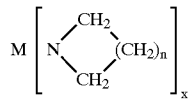

wherein M is selected from the group consisting of: Zr, Hf, Y, La, Lanthanide series elements, Ta, Ti, Al; N is nitrogen; each of $R^1$ and $R^2$ is same or different and is independently selected from the group consisting of H, aryl, perfluoroaryl, $C_1$–$C_8$ alkyl, $C_1$–$C_8$ perfluoroalkyl, alkylsilyl; and x is the oxidation state on metal M; and n is from 1–6.

In a preferred embodiment, M is Zr or Hf, and $R^1$ and $R^2$ are methyl and/or ethyl. In a more preferred embodiment, the metalloamide source reagents useful for depositing dielectric thin films on a substrate include but are not limited to, compounds of the formula $M(NMe_2)_x$, $M(NEt_2)_x$, $M(NMeEt)_x$.

Examples of metalloamide compounds which may be usefully employed in the present invention include, without limitation, $Zr(NMe_2)_4$, $Zr(NMeEt)_4$, $Zr(NEt_2)_4$, $Ta(NEt_2)_5$, $Ta(NMe_2)_5$, $Ta(NMeEt)_5$, $Zr(NiPr_2)_4$, $Zr(NMe_2)_2(NPr_2)_2$, $Zr(NC_6H_{12})_4$, $Zr(NEt_2)_2(NPr_2)_2$, $Hf(NEt_2)_4$, $Hf(NMe_2)_4$, $Hf(NMeEt)_4$, $La(NMe_2)_3$, $La(NEt_2)_3$, $La(NMeEt)_3$, $Al(NMe_2)_3$, $Al(NEt_2)_3$, $Y(NMe_2)_3$, $Y(NEt_2)_3$, $Y(NMeEt)_3$, $Ti(NMe_2)_4$, $Ti(NEt_2)_4$, $Ti(NMeEt)_4$, $Ta(NMe_2)_5$, $Ta(NEt_2)_5$, wherein Me represents methyl, Et represents ethyl, Pr represents propyl, and iPr represents isopropyl. Preferred metalloamide source reagent compounds useful in the present invention include $Zr(NMe_2)_4$, $Zr(NEt_2)_4$, $Hf(NEt_2)_4$ and $Hf(NMe_2)_4$.

In a specific embodiment, the metalloamide source reagent compound useful in the present invention may comprise an oligomer, i.e. $Al_2(\mu\text{-}NMe_2)_2(NMe_2)_4$.

The metalloamide source reagents of the present invention are useful for forming dielectric thin films including but not limited to: gate dielectrics, high dielectric constant metal oxides, and ferroelectric metal oxides.

In one embodiment, the metalloamide source reagents are useful for forming gate dielectric thin films on a substrate, wherein the gate dielectric thin film may comprise a metal-oxide, a metal oxy-nitride, a metal silicate or a metal silicon-oxy-nitride. More preferably, the metalloamide source reagent is useful for forming a metal silicate gate dielectric thin film.

In a further embodiment, the present invention relates to a CVD precursor composition for forming a thin film dielectric on a substrate, such precursor composition including at least one aminosilane source reagent compound selected from the group consisting of:

$H_xSiA_y(NR^1R^2)_{4-x-y}$; and

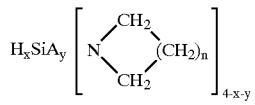

wherein H is hydrogen; x is from 0 to 3; Si is silicon; A is a halogen; Y is from 0 to 3; N is nitrogen; each of $R^1$ and $R^2$ is same or different and is independently selected from the group consisting of H, aryl, perfluoroaryl, $C_1$–$C_8$ alkyl, and $C_1$–$C_8$ perfluoroalkyl; and n is from 1–6. Preferably, $R^1$ and $R^2$ are methyl and/or ethyl.

In a preferred embodiment, the aminosilane source reagent compounds useful for depositing a dielectric thin film on a substrate include but are not limited to: $Si(NMe_2)_3Cl$, $Si(NEt_2)_2Cl_2$, $Si(NMe_2)_4$, and $Si(NEt_2)_4$.

The aminosilane source reagent compound may be used to deposit silicate or silicon oxy-nitride gate dielectric thin films on a substrate or the aminosilane source reagent may be used in combination with the metalloamide source reagent composition, as described hereinabove, to deposit a metal silicate or metal silicon-oxy-nitride gate dielectric thin film on a substrate.

The invention in a further embodiment relates to a CVD precursor composition for forming a thin film dielectric on a substrate, such precursor composition including a metalloamide vapor source reagent compound selected from the group consisting of:

$M(NR^1R^2)_x$; and

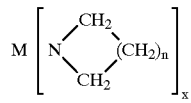

wherein M is selected from the group consisting of: Zr, Hf, Y, La, Lanthanide series elements, Ta, Ti, Al; N is nitrogen; each of $R^1$ and $R^2$ is same or different and is independently selected from the group consisting of H, aryl, perfluoroaryl, $C_1$–$C_8$ alkyl, $C_1$–$C_8$ perfluoroalkyl, alkylsilyl; x is the oxidation state on metal M; and n is from 1–6.

In a further embodiment the present invention relates to a CVD precursor composition for forming a thin film dielectric on a substrate, such precursor composition including at least one aminosilane vapor source reagent compound selected from the group consisting of:

$H_xSiA_y(NR^1R^2)_{4-x-y}$; and

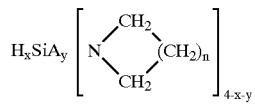

wherein H is hydrogen; x is from 0 to 3; Si is silicon; A is a halogen; Y is from 0 to 3; N is nitrogen; each of $R^1$ and $R^2$ is same or different and is independently selected from the group consisting of H, aryl, perfluoroaryl, $C_1$–$C_8$alkyl, and $C_1$–$C_8$ perfluoroalkyl; and n is from 1–6.

In a preferred embodiment, $R^1$ and $R^2$ are methyl and/or ethyl. In a more preferred embodiment, the aminosilane vapor source reagent compounds usefully employed in the present invention include, without limitation, $Si(NMe_2)_3Cl$, $Si(NEt_2)_2Cl_2$, $Si(NMe_2)_4$, and $Si(NEt_2)_4$.

In one embodiment of the present invention the metalloamide CVD precursor composition is used to deposit a silicate gate dielectric thin film wherein the metalloamide precursor is suitably used in combination with a silicon precursor(s) source to yield the product metal silicate film. The silicon precursor may advantageously comprise an aminosilane source reagent compound as described herein or may alternatively comprise an alternative silicon source reagent compound as known to those skilled in the art, to deposit silicate thin films, (e.g. silane, trimethylsilane, tetramethylsilane and tetraethylorthosilicate).

In a further embodiment of the present invention the metalloamide CVD precursor composition is bi-functional in that it may be used to deposit a gate dielectric thin film and a gate conductor, wherein the gate dielectric thin film is first deposited on a substrate using CVD conditions as described herein followed by deposition of a gate conductor on the gate dielectric substrate. The bi-functional nature of the metalloamide source reagent compound is advantageous in that it limits the number of process steps necessary to produce two components of a device structure. As an example, in a first step, a (Hf, Si)$O_4$ gate dielectric thin film is CVD deposited on a substrate from Hf(NMe$_2$)$_4$, Si(NMe$_2$)$_4$ and $N_2O$ process gas. In a second step, a HfN gate conductor is deposited on the (Hf, Si)$O_4$ gate dielectric thin film of step one, from Hf(NMe$_2$)$_4$ and $NH_3$ process gas. This is especially useful for NMOS, where the fermi level of the gate conductor should be well matched to that in the channel.

By utilizing a precursor composition including at least one metalloamide source reagent compound and at least one aminosilane source reagent compound, to produce a metal silicate dielectric thin film on a substrate, with the metalloamide source reagent compound containing at least part of the metal to be incorporated in the product dielectric metal silicate film, and the aminosilane source reagent compound containing at least part of the silicon to be incorporated in the product dielectric metal silicate film, it is possible by selection of the proportions of such respective compounds to correspondingly vary the stoichiometric composition (metal/silicon ratio) of the metal silicate dielectric film, to obtain a desired character of structural and performance properties in the product film. For example, an aminosilane source reagent compound, containing no metal, may be used in combination with a metalloamide source reagent compound, containing no silicon, to control film ratios, (i.e., Zr/Si or Hf/Si).

In one embodiment, the present invention relates to a CVD precursor composition for forming a silicate thin film dielectric on a substrate, such precursor including a vapor source mixture comprising at least one metalloamide vapor source reagent compound as described hereinabove and at least one aminosilane vapor source reagent compound as described hereinabove, wherein the relative proportions of the aminosilane vapor source reagent and the metalloamide vapor source reagent relative to one another are employed to controllably establish the desired $M_x/Si_{1-x}$ ratio in the deposited silicate thin films, wherein $M_x/Si_{1-x}$ is from about 0.01 to 10. The exact composition will be a trade off between high Si films, which prevent crystallization during subsequent high temperature processing, and high M films, which have higher dielectric constant (lower EOT).

In a further embodiment the present invention relates to a CVD precursor solution composition for forming a thin film dielectric on a substrate, such precursor composition including at least one metalloamide compound as described hereinabove and a solvent medium in which the metalloamide compound is soluble or suspendable, wherein the metalloamide compound and the solvent medium are combined to produce a precursor solution mixture for depositing a dielectric thin film on a substrate.

In a further embodiment the present invention relates to a CVD precursor solution composition for forming a thin film dielectric on a substrate, such source reagent composition including at least one aminosilane compound as described hereinabove and a solvent medium in which at least one aminosilane compound is soluble or suspendable, wherein the aminosilane precursor compound and the solvent medium are combined to produce a precursor solution mixture for depositing a silicon containing dielectric thin film on a substrate.

In a further embodiment, the present invention relates to a CVD multi-component, single source precursor composition useful for forming a thin film dielectric on a substrate, such source composition including at least one metalloamide compound as described hereinabove, at least one aminosilane compound as described hereinabove and a solvent medium in which the metalloamide compound and the aminosilane compound are soluble or suspendable, wherein the metalloamide source reagent compound, the aminosilane compound, and the solvent medium are combined to produce a chemically compatible, single source solution mixture for depositing a silicon containing dielectric thin film on a substrate.

Providing a precursor composition in liquid (i.e., neat solution or suspension) form facilitates rapid volatilization (i.e., flash vaporization) of the source reagent composition and transport of the resultant precursor vapor to a deposition locus such as a CVD reaction chamber. The metalloamide and aminosilane compounds of the present invention are chosen to provide a degenerate sweep of ligands, to eliminate ligand exchange and to provide a robust precursor delivery, gas-phase transport and CVD process.

The precursor compositions of the present invention may comprise any suitable solvent medium that is compatible with the metalloamide and/or aminosilane compounds contained therein. The solvent medium in such respect may comprise a single component solvent, or alternatively a solvent mixture or solution. Illustrative solvent media that may be variously usefully employed include ethers, glymes, tetraglymes, amines, polyamines, aliphatic hydrocarbon solvents, aromatic hydrocarbon solvents, cyclic ethers, and compatible combinations of two or more of the foregoing. A particularly preferred solvent species useful in the practice of the present invention is octane.

The source reagent compounds of the invention are stable, even in organic solutions, while at the same time they are volatilizable at low temperatures that are consistent with efficient chemical vapor deposition processing. The source reagent compounds of the present invention also possess the following advantageous features: good deposition rates; good thermal stability; higher elemental purity; formation of essentially carbon-free films (in contrast to the reported literature, i.e. Jones, et al., "MOCVD of Zirconia Thin Films by Direct Liquid Injection Using a New Class of Zirconium Precursor", *Chem. Vap. Dep.*, Vol. 4, 1998, PP. 46–49.); limited $SiO_2$ interlayer formation; ready decomposition at CVD process temperatures; and good solubility in a wide variety of organic solvents and solvent media.

Here and throughout this disclosure, where the invention provides that at least one aminosilane compound and one metalloamide compound are present in a composition or method, the composition or method may contain or involve additional, (i.e., third and fourth) metalloamide and/or aminosilane compounds.

The metalloamide and aminosilane source reagent compounds of the invention and methods of making are well known in the art and may be obtained from commercial sources or readily prepared by published synthetic routes. See, D. C. Bradley and I. M. Thomas, "Metalorganic Compounds Containing Metal-Nitrogen Bonds: Part I. Some Dialkylamino Derivatives of Titanium and Zirconium", *J. Chem. Soc.*, 1960, 3857) (D. C. Bradley and I. M. Thomas, "Metalorganic Compounds Containing Metal-Nitrogen Bonds: Part III. Dialkylamino Compounds of Tantalum", *Canadian J. Chem.*, 40, 1355 (1962). Many of the metalloamide and aminosilane source reagent compounds of the present invention are available commercially through ATMI, Inc., Inorgtech, Gelest, Inc., Aldrich Chemical Company and Strem Chemical Company.

In a further embodiment the present invention relates to a method for forming a dielectric thin film on a substrate by chemical vapor deposition.

Such method includes the steps of:
vaporizing a precursor composition comprising at least one metalloamide source reagent compound selected from the group consisting of:

$M(NR^1R^2)_x$; and

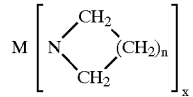

wherein M is selected from the group consisting of: Zr, Hf, Y, La, Lanthanide series elements, Ta, Ti, Al; N is nitrogen; each of $R^1$ and $R^2$ is same or different and is independently selected from the group consisting of H, aryl, perfluoroaryl, $C_1$–$C_8$ alkyl, $C_1$–$C_8$ perfluoroalkyl, alkylsilyl; and x is the oxidation state on metal M; and n is from 1–6;
, as described hereinabove, to form a source reagent precursor vapor,
transporting such source reagent precursor vapor into a chemical vapor deposition zone containing a substrate, optionally using a carrier gas to effect such transport;
contacting the source reagent precursor vapor with a substrate in such chemical vapor deposition zone in the presence of an oxidizer and at elevated temperature to deposit a corresponding M containing dielectric thin film.

In a further embodiment the present invention relates to a method for forming a dielectric silicate thin film on a substrate by chemical vapor deposition.

Such method includes the steps of:
vaporizing a precursor composition comprising at least one aminosilane compound selected from the group consisting of:

$H_xSiA_y(NR^1R^2)_{4-x-y}$; and

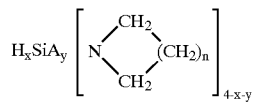

as described hereinabove, to form a source reagent precursor vapor;
transporting such source reagent precursor vapor into a chemical vapor deposition zone containing a substrate, optionally using a carrier gas to effect such transport;
contacting the source reagent precursor vapor with a substrate in such chemical vapor deposition zone in the presence of an oxidizer and at elevated temperature to deposit a corresponding Si containing dielectric thin film.

The metalloamide and aminosilane compounds of the present invention may be used independently or in combination to form the desired dielectric thin film. When used in combination, the metalloamide and aminosilane compound may be vaporized and deposited simultaneously or sequentially to obtain a dielectric thin film having the desired property.

The particular CVD method used to deposit the dielectric thin films of the present invention may be one of many known to those skilled in the art. Particularly preferred CVD methods for delivery and deposition of the metalloamide and aminosilane source reagent compounds of the present invention include liquid delivery chemical vapor deposition (LDCVD) and atomic layer chemical vapor deposition (ALCVD).

In an atomic layer chemical vapor deposition embodiment, a metalloamide precursor vapor is introduced into a chemical vapor deposition chamber comprising a substrate, in a sequential or "pulsed" deposition mode, during which time, extremely co-reactive gases may be employed, such as ozone, water vapor or reactive alcohols, that might normally be expected to produce deleterious deposition effects on the CVD process (i.e., gas phase particle formation).

In a further embodiment, the atomic layer chemical vapor deposition method of the present invention, may further comprise an aminosilane precursor vapor that may be simultaneously co-pulsed and co-deposited with the metalloamide precursor vapor, on a substrate. Alternatively, the aminosilane precursor vapor may be deposited on a substrate in a sequential pulsing method, wherein the aminosilane compound alternates pulses with the metalloamide compound. The dielectric thin films are built up by introducing short bursts of gases in cycles.

In a further embodiment, a co-reactant may be used in a pulsed or atomic layer chemical vapor deposition method, wherein the metalloamide precursor and/or aminosilane precursor vapor is separated from the co-reactant by time in the pulse track. The co-reactant may be utilized to facilitate the decomposition of the precursor on a substrate, within a desired temperature regime and to produce carbon-free dielectric thin-films. As an example, the use of water vapor may be utilized to induce a lower decomposition temperature of the aminosilane precursor vapor, which in some instances has been found to be stable in oxidizing environments such as $N_2O$.

The specific nature of the pulse track and number of cycles may be varied. In a typical ALCVD process, a cycle lasts from 1–5 seconds. The following non-limiting examples demonstrate various pulse tracks defining precursor(s) and co-reactant(s) that may be successfully used to deposit the dielectric thin films of the present invention:
example track 1—(metalloamide/purge (inert)/co-reactant+ $N_2O$/purge (inert))n cycles;
example track 2—(metalloamide+aminosilane/purge (inert)/ $N_2O$/purge (inert))n cycles;
example track 3—(metalloamide+co-reactant $N_2O$/co-reactant water vapor/purge (inert))n cycles;
example track 4—(metalloamide+co-reactant $N_2O$/ aminosilane/co-reactant water vapor/purge (inert))n cycles.
wherein n is an integer number, typically ranging from 10 to 100, and different co-reactants have different oxidizing potentials.

In liquid delivery CVD, the source liquid may comprise the source reagent compound(s) if the compound or complex is in the liquid phase at ambient temperature (e.g., room temperature, 25° C.) or other supply temperature from which the source reagent is rapidly heated and vaporized to form precursor vapor for the CVD process. Alternatively, if the source reagent compound or complex is a solid at ambient or the supply temperature, such compound or complex can be dissolved or suspended in a compatible solvent medium therefore to provide a liquid phase composition that can be submitted to the rapid heating and vaporization to form precursor vapor for the CVD process. The precursor vapor resulting from the vaporization then is transported, optionally in combination with a carrier gas (e.g., He, Ar, $H_2$, $O_2$, etc.), to the chemical vapor deposition reactor where the vapor is contacted with a substrate at elevated temperature to deposit material from the vapor phase onto the substrate or semiconductor device precursor structure positioned in the CVD reactor.

The precursor liquid may be vaporized in any suitable manner and with any suitable vaporization means to form corresponding precursor vapor for contacting with the elevated temperature substrate on which the dielectric film is to be formed. The vaporization may for example be carried out with a liquid delivery vaporizer unit of a type as commercially available from Advanced Technology Materials, Inc. (Danbury, Conn.) under the trademark SPARTA and VAPORSOURCE II, in which precursor liquid is discharged onto a heated vaporization element, such as a porous sintered metal surface, and flash vaporized. The vaporizer may be arranged to receive a carrier gas such as argon, helium, etc. and an oxygen-containing gas may be introduced as necessary to form the dielectric thin film. The precursor vapor thus is flowed to the chemical vapor deposition chamber and contacted with the substrate on which the dielectric film is to be deposited. The substrate is maintained at a suitable elevated temperature during the deposition operation by heating means such as a radiant heating assembly, a susceptor containing a resistance heating element, microwave heat generator, etc. Appropriate process conditions of temperature, pressure, flow rates and concentration (partial pressures) of metal and silicon components are maintained for sufficient time to form the dielectric film at the desired film thickness, (i.e., in a range of from about 2 nanometers to about 1000 micrometers), and with appropriate dielectric film characteristics.

The step of vaporizing the source reagent compounds of the present invention is preferably carried out at a vaporization temperature in the range of from about 50° C. to about 300° C. Within this narrow range of vaporization temperature, the metalloamide and aminosilane source reagent compounds are effectively vaporized with a minimum extent of premature decomposition.

In the optional use of a carrier gas in the practice of the present invention, for transporting the vaporized source reagent composition into the chemical vapor deposition zone, suitable carrier gas species include gases that do not adversely affect the dielectric film being formed on the substrate. Preferred gases include argon, helium, krypton or other inert gas, with argon gas generally being most preferred. In one illustrative embodiment, argon gas may be introduced for mixing with the vaporized source reagent composition at a flow rate of about 100 standard cubic centimeters per minute (sccm).

Oxidizing gases useful for the broad practice of the present invention include, but are not limited to, $O_2$, $N_2O$, NO, $H_2O$ and O3, More preferably, the oxidizer used comprises $N_2O$.

The deposition of the dielectric thin films of the present invention are preferably carried out under an elevated deposition temperature in a range of from about 250° C. to about 750° C.

By way of example, $Hf(NMe_2)_4$ and $Si(Me)_4$ may be mixed in a gas stream, (i.e., in a carrier gas), and mixed in the gas stream to the CVD reactor to produce the appropriate stoichiometry in a deposited $HfSiO_4$ thin-film. Other metalloamides of the invention and silanes may be similarly employed with equivalent success, provided that the respective ligands do not produce undesirable non-degenerate ligand exchanges forming (undesired) new precursor species. It therefore is preferred to use the same ligand species, (ie., methyl, ethyl, phenyl, etc.) for each of the metalloamide and silicon precursors used in combination with one another.

By way of further example, $Hf(NMe_2)_4$ and $Si(NMe_2)_4$ may be mixed in a gas stream, (ie., in a carrier gas), and mixed in the gas stream to the CVD reactor to produce the appropriate stoichiometry in a deposited $Hf_xSi_{2-x}O_4$ thin-film, wherein x is from 0 to 1. Other metalloamides of the invention and aminosilanes may be similarly employed with equivalent success, provided that the respective ligands do not produce undesirable non-degenerate ligand exchanges forming (undesired) new precursor species. It therefore is preferred to use the same ligand species, (i.e., methyl, ethyl, phenyl, etc.) for each of the metalloamide and aminosilane precursors used in combination with one another.

By way of further example, a representative liquid delivery chemical vapor deposition approach is illustrated by the use of metalloamide source reagent compound, $Zr(NMe_2)_4$ and aminosilane source reagent compound $Si(NMe_2)_4$. The source reagent compounds are introduced into a chemical vapor deposition chamber using liquid delivery and oxidized in-situ to deposit on a substrate, the desired Zr silicate thin film composition based upon electrical performance and film stoichiometry. $La(NMe_2)_3$ may be added to the mixture to produce a Zr La doped silicate dielectric film under similar processing conditions.

By way of further example, a representative liquid delivery chemical vapor deposition approach is illustrated by the use of metalloamide source reagent compound, $Y(NMe_2)_3$ and aminosilane source reagent compound $Si(NEt_2)_4$ The source reagent compounds are introduced into a chemical vapor deposition chamber using liquid delivery and oxidized in-situ to deposit on a substrate, the desired Y silicate thin film composition based upon electrical performance and film stoichiometry.

By way of further example, a representative liquid delivery chemical vapor deposition approach is illustrated by the use of metalloamide source reagent compounds $Hf(NMe_2)_4$ and $La(NMe_2)_3$ and aminosilane source reagent compound $Si(NEt_2)_4$. The source reagent compounds are introduced into a chemical vapor deposition chamber using liquid delivery and oxidized in-situ to deposit on a substrate, the desired HfLa silicate thin film composition based upon electrical performance and film stoichiometry. $Zr(NMe_2)_4$ may be added to the mixture to produce Zr doped silicate films under similar processing conditions.

As evidenced hereinabove, it is possible to use respective metalloamides and aminosilane compounds, (i.e., alkyl, and phenyl compounds), regardless of ligand identity and ligand exchange mechanisms, by the use of techniques such as atomic layer or pulsed CVD method, in which the incompatible precursors are separated both temporally and in the introduction lines to limit particle formation and undesired ligand exchange reactions.

In a further embodiment, the present invention relates to a dielectric thin film, having a dielectric constant value in a range between about 4 to about 60 as measured at a frequency of 1 mega-Hertz, produced by a method comprising the steps of:

vaporizing a precursor composition comprising at least one metalloamide compound selected from the group consisting of:

$M(NR^1R^2)_x$; and

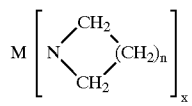

as described hereinabove, to form a source reagent precursor vapor;

transporting such source reagent precursor vapor into a chemical vapor deposition zone containing a substrate, optionally using a carrier gas to effect such transport;

contacting the source reagent precursor vapor with a substrate in such chemical vapor deposition zone in the presence of an oxidizer and at elevated temperature to deposit a corresponding M containing dielectric thin film.

In a further embodiment the present invention relates to a silicon containing dielectric thin film, having a dielectric constant in a range between about 4 to about 60 as measured at a frequency of 1 mega-Hertz, by a method comprising the steps:

vaporizing a source reagent precursor composition comprising at least one aminosilane compound selected from the group consisting of:

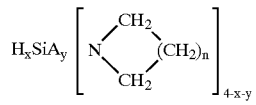

as described hereinabove, to form a source reagent precursor vapor;

transporting such source reagent precursor vapor into a chemical vapor deposition zone containing a substrate, optionally using a carrier gas to effect such transport;

contacting the source reagent precursor vapor with a substrate in such chemical vapor deposition zone in the presence of an oxidizer and at elevated temperature to deposit a corresponding silicate dielectric thin film.

The dielectric metal silicate thin films produced from the metalloamide materials of the present invention are pure metal silicate thin films comprising little or no carbon or halogen impurity. In a preferred embodiment the dielectric silicate thin films contain less than 1 atomic percent carbon and more preferably the thin films contain less than 1 ppm carbon and no detectable halogen.

The dielectric silicate films produced in the broad practice of the invention include stoichiometric metal silicate films, as well as off-stoichiometric (metal-deficient) films. Where the precursor composition includes different source reagents providing respectively differential metal and/or silicon content, then the respective source reagents can be supplied in varied compositions to achieve desired stoichiometric characteristics in the corresponding product metal silicate films. In this manner, the electrical properties, including dielectric constant and leakage, can be controlled and closely tailored to a desired end use.

The dielectric thin films produced by a method of the present invention are useful as, but not limited to: gate dielectric thin films, more particularly metal silicate gate dielectric thin films and metal oxy-nitride gate dielectric thin films; metal oxide high dielectric thin films; and ferroelectric thin films.

The presence of nitrogen, in at least a partial thickness of the gate dielectric helps to prevent the diffusion of boron, such as from a boron-doped polysilcon gate electrode, to the channel region.

Exemplary dielectric thin films formed by the method of the present invention include but are not limited to: $ZrSiO_4$; $HfSiO_4$; $Ta_{1-x}Al_xO_y$, where x is 0.03–0.7 and y is 1.5–205; $Ta_{1-x}Si_xO_y$, where x is 0.05–0.15 and y is 1.5–3; $Ta_{1-x-z}Al_xSi_zO_y$, where 0.7>x+z>0.05, z<0.15 and y is 1.5–3; $HfO_2$; $ZrO_2$; $Ta_2O_5$; $Zr_xSi_{2-x}O_4$ where x is 0.2–1.6; $Hf_xSi_{2-x}O_4$, where x is 0.2–1.6; $Hf_xLa_ySi_{2-x}O_{4+1.5y}$, where x is 0.2–1.6 and y is 0–1; $Zr_xLa_ySi_{2-x}O_{4+1.5y}$, where x is 0.2–1.6 and y is 0–1; $Hf_xAl_ySi_{2-x}O_{4+1.5y}$, where x is 0.2–1.6 and y is 0–0.2; $Zr_xAl_ySi_{2-x}O_{4+1.5y}$, where x is 0.2–1.6 and y is 0–0.2.

The features, aspects and advantages of the present invention are further shown with reference to the following non-limiting examples relating to the invention.

EXAMPLES

Process and Chemistry for Deposition of Hafnia Films from Alkylamido Precursors $HfO_2$ is a component of many of the proposed alternative high k gate dielectrics. One of the issues in growing a gate dielectric by a CVD process is minimizing the growth of interfacial $SiO_2$. There is some evidence that interfacial $SiO_2$ will grow even if the only oxygen present in the process is in an oxygen-containing precursor, such as an alkoxide or a mixed alkoxide-β-diketonate. In order to avoid this possibility, the viability of alkyl-amido Hf, specifically, $Hf(NMe_2)_4$ and $Hf(NEt_2)_4$ hereafter referred to as TDMAHf and TDEAHf, respectively, has been studied.

Carbon-free $HfO_2$ can be grown at high deposition rates from these precursors at temperatures down to 400° C. in an ambient of $N_2O$. It is quite unexpected that $N_2O$ is effective at oxidizing the precursor at such low temperatures and there is no sign of the process getting worse at lower temperatures either with increase carbon or lower deposition rate.

The results described herein are extendable to the growth of a wide range of oxide films at low temperatures. Notably, $Ta_2O_5$ and doped $Ta_2O_5$ might also grow as clean amorphous films at low temperatures from alkylamido precursors in $N_2O$.

Experiment

Figure 2A:
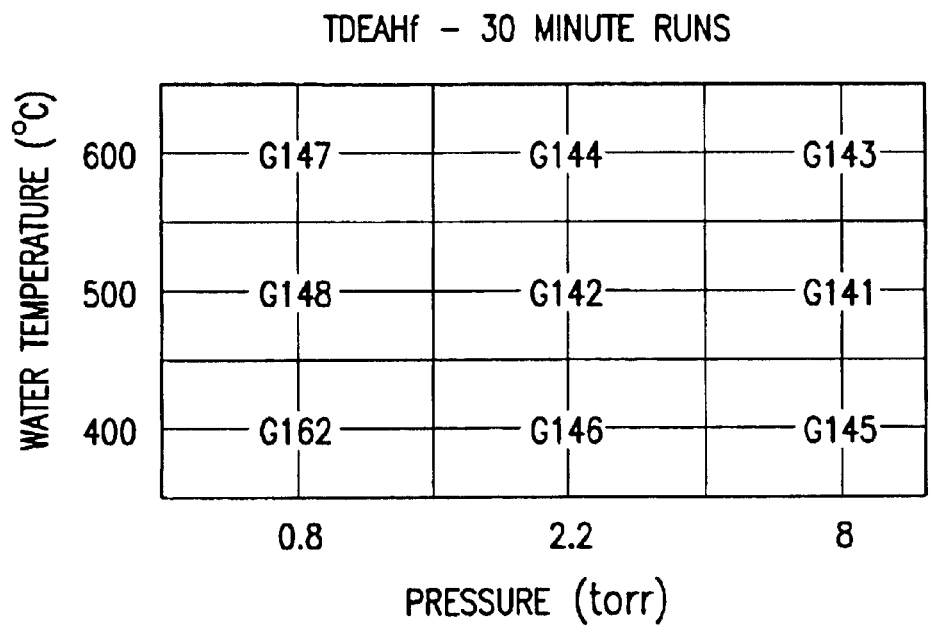
FIG. 2A and FIG. 2B show a pressure temperature matrix for $Hf(N(C_2H_5)_2)_4$ (Tetrakis(diethyl-amino)hafnium) and $Hf(N(CH_3)_2)_4$ (Tetrakis(dimethyl-amino)hafnium) in $N_2O$.
Figure 2B:
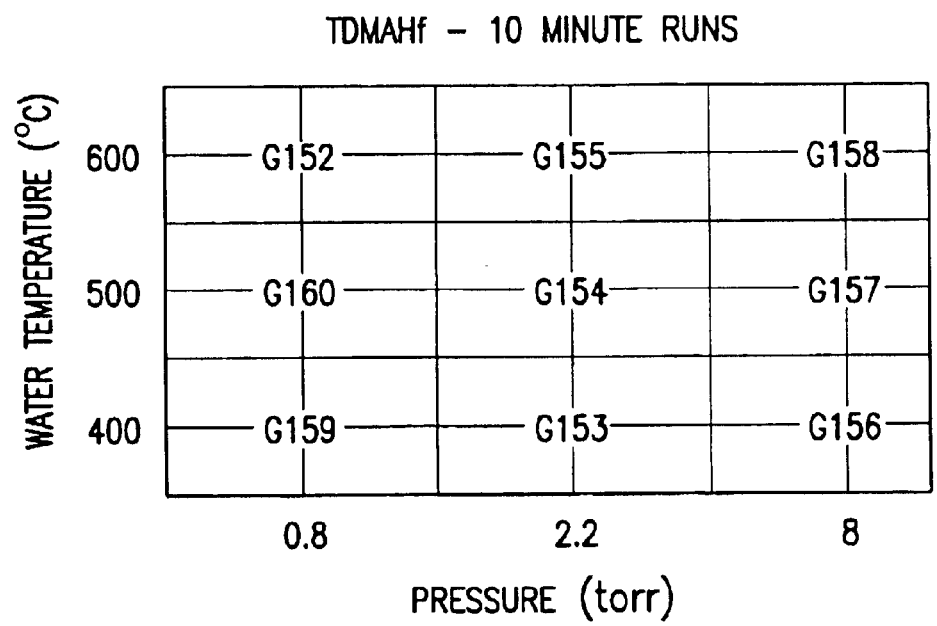

Hafnia films were grown with the precursors listed in Table I. Precursor solutions were prepared at 0.1M Hf in octane. Substrate of (100) Si was prepared with an SC1 treatment followed by dilute HF to remove any $SiO_2$ on the surface. The generic process conditions for the experiments are shown in Table II. Initially, films were grown at 550° C. under three different reactive gas conditions: Ar, $N_2O$ and $O_2$. Results described below indicated that $N_2O$ was the preferred ambient. A pressure-temperature matrix was performed for each precursor using the $N_2O$ ambient as shown in FIGS. 2A and 2B. FIGS. 2A and 2B show the process space experiments for TDEAHf and TDMAHf precursors. At the end, a film targeting 50 Å was grown from each precursor to be used for TEM examination of the interface with Si.

TABLE I

Precursors used for film deposition.

| | | |
|---|---|---|
| Tetrakis(diethyl-amino)hafnium | $Hf(N(C_2H_5))_4$ | TDEAHf |
| Tetrakis(dimethyl-amino)hafnium | $Hf(N(CH_3))_4$ | TDMAHf |

TABLE II

Generic process conditions for zirconia and hafnia films

| | |
|---|---|
| Precursor solution | 0.10 M in octane |
| Precursor solution delivery rate | 0.10 ml/min |
| Vaporization Temperature | 150° C. |
| Run time | 10–30 minutes |
| Carrier gas | 100 sccm Ar |
| Heating and Cooling process gas | 500 sccm Ar |
| Run time process gas | 400 sccm $N_2O$ or $O_2$ |
| Pressure | 0.8, 2.2, or 8.0 Torr |
| Temperature | 400–600° C. wafer surface |

Film thickness was measured using single-wavelength ellipsometry at 70° incidence angle, and XRF. For $HfO_2$, the XRF was calibrated by assuming the X-ray efficiencies were equivalent to $TaO_{2.5}$, for which we have standards that have been measured by RBS.

Results

Figure 3:
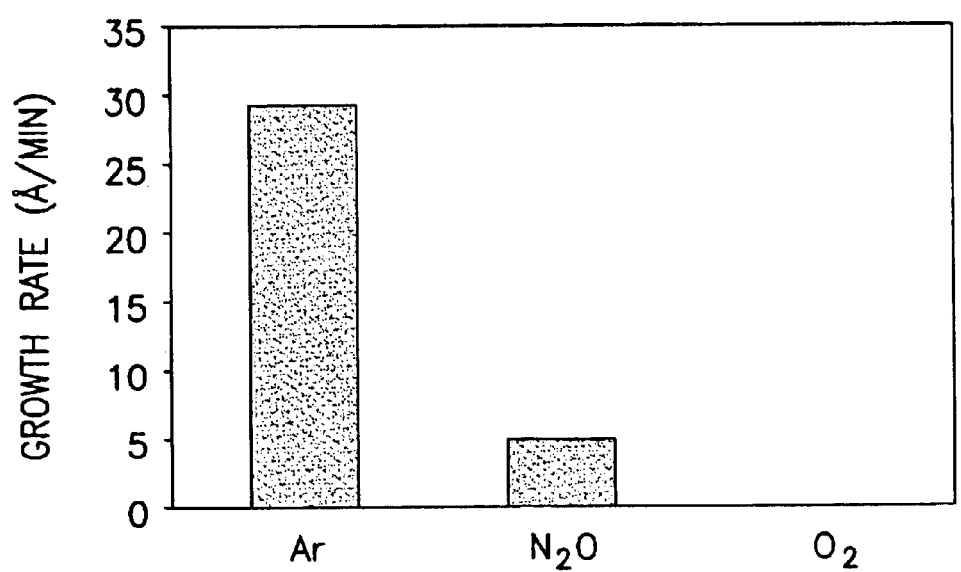
FIG. 3 shows the growth rate of hafnia films in different oxidizing ambients at 8 Torr and 550° C.

The growth rate of hafnia was measured by XRF for films grown in different oxidizing ambients at 8 Torr and 550° C. as shown in FIG. 3. The compositions of these films were measured by XPS. The films grown in the inert Ar environment had a high growth rate, but this growth was accompanied by considerable carbon and some nitrogen incorporation. Films grown in $N_2O$ were surprisingly carbon-free, but with a low growth rate. No film growth was detected for the run performed in $O_2$. With these results, further examination of pressure and temperature were performed in a $N_2O$ ambient.

Figure 4A:
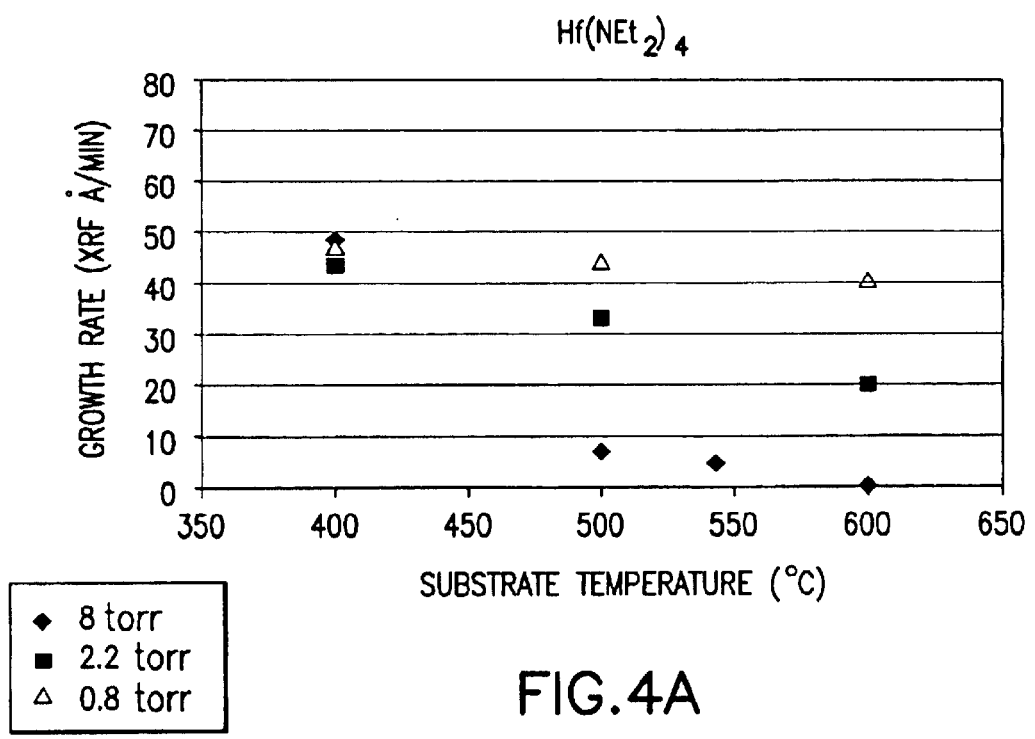
FIGS. 4A and 4B show growth rate over process space for $Hf(N(C_2H_5)_2)_4$ (Tetrakis(diethyl-amino)hafnium) and $Hf(N(CH_3)_2)_4$ (Tetrakis(dimethyl-amino)hafnium.
Figure 4B:
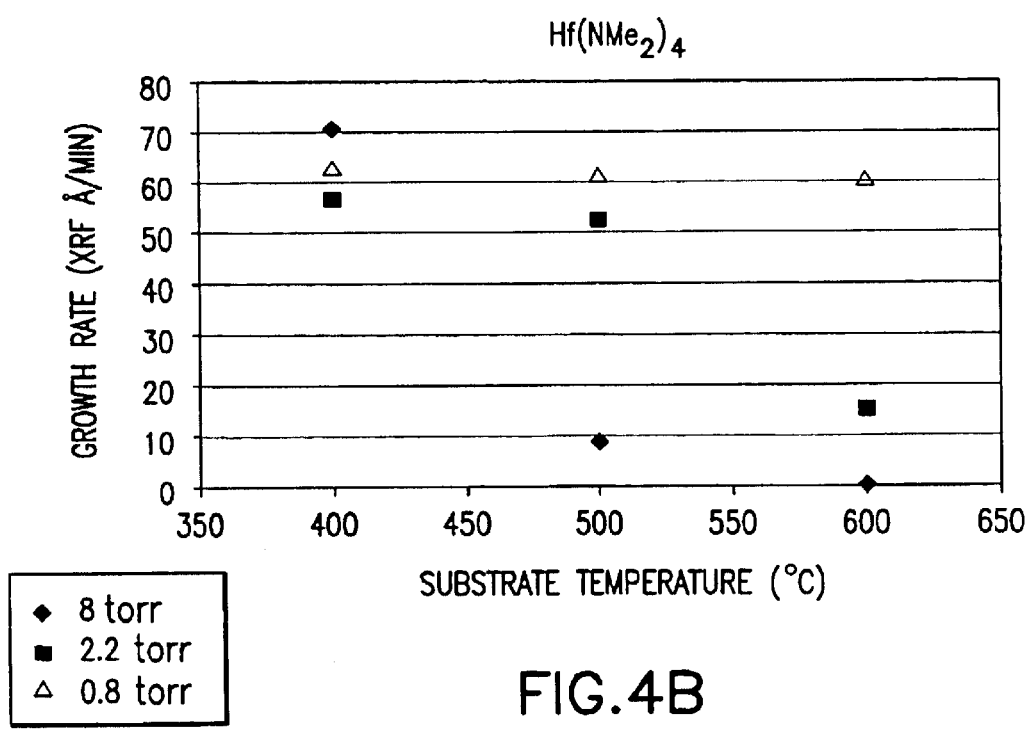

The growth rate as measured by XRF varied over process space for the two precursors as shown in FIGS. 4A and 4B. For both precursors, the growth rate is low at higher temperatures and pressures. At the 0.8 Torr, growth rate is largely independent of temperature, and at 400° C. the growth rate is largely independent of pressure. The growth rate of TDEAHf is slightly lower than TDMAHf, but both have rates that are sufficient for manufacturable deposition.

Figure 5:
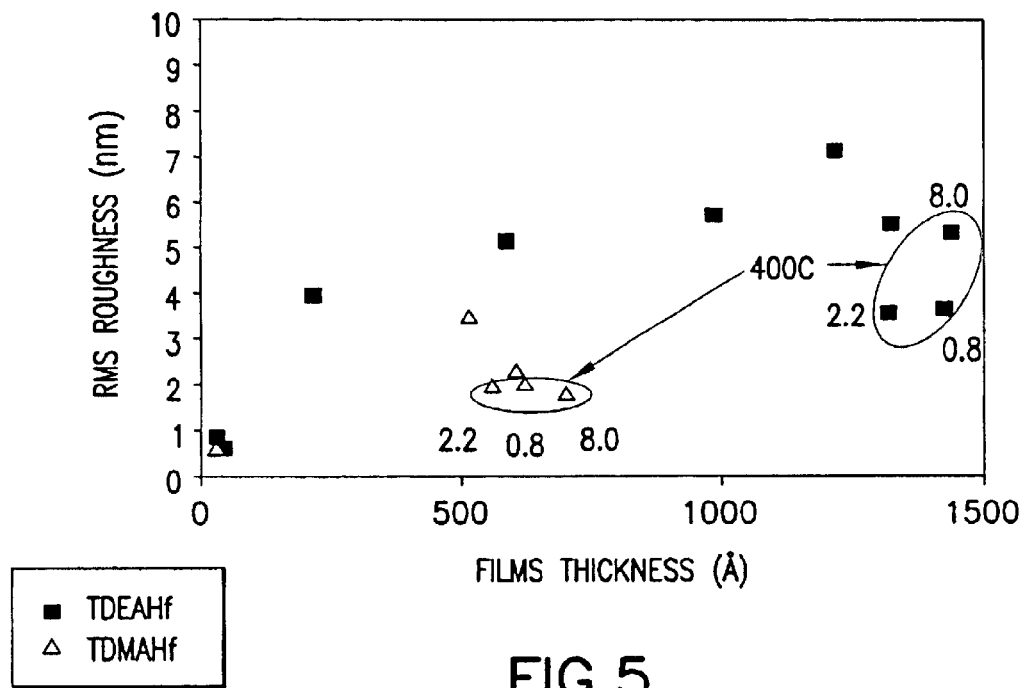
FIG. 5 shows RMS roughness as measured by AFM over 1×1 $\mu m$ areas of $Hf(N(C_2H_5)_2)_4$ (Tetrakis(diethyl-amino)hafnium) and $Hf(N(CH_3)_2)_4$ (Tetrakis(dimethyl-amino)hafnium) thin films.

The RMS roughness of the films was measured by AFM over a 1×1 μm areas and the results plotted as a function of film thickness as shown in FIG. 5. Films generally roughen somewhat as they become thicker, so that it is important to compare their morphology to others of the same thickness. For both precursors, films grown at 400° C. are smoother than those grown at higher temperatures. The growth time was shorter for the TDMAHf films, so they were much thinner and also smoother. A film was grown for each precursor to a thickness of about 50 Å. In both cases, the RMS roughness was about 6 Å.

Figure 6:
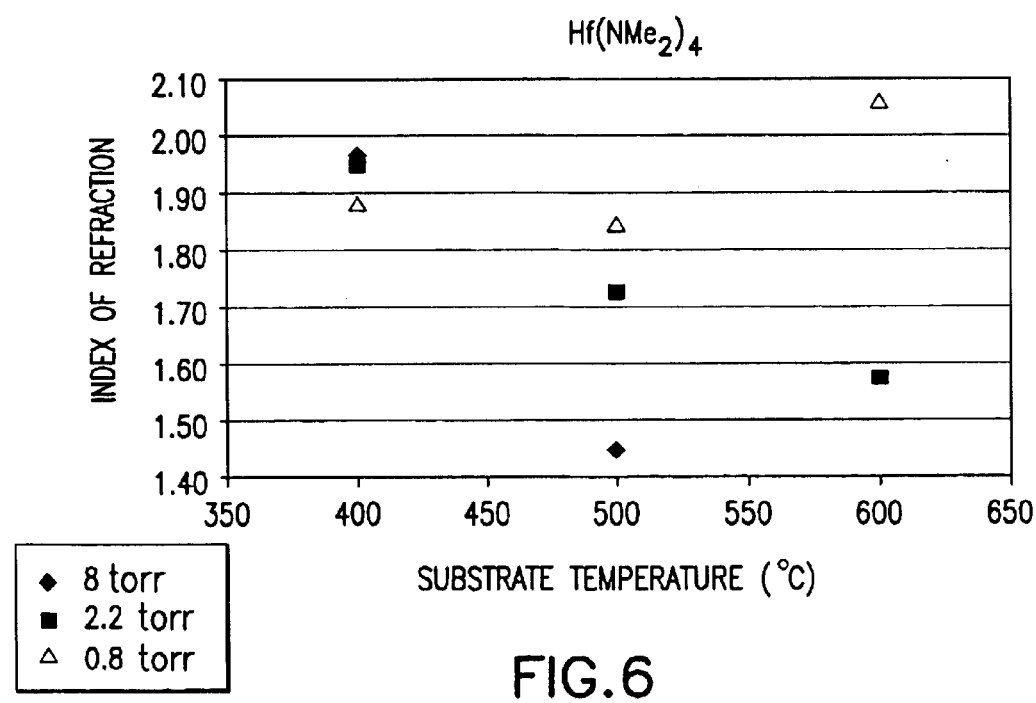
FIG. 6 shows index of refraction measurements as a function of process conditions for $Hf(N(CH_3)_2)_4$ (Tetrakis(dimethyl-amino)hafnium) thin films.

Film thickness and index of refraction were measured by ellipsometry for all films. Those grown from TDEAHf were thick and the resulting roughness prevented reliable ellipsometry measurements. The index of refraction of the films grown from TDMAHf is shown as a function of process condition in FIG. 6. The films grown at lower temperature exhibited higher refractive index, which probably indicates either a more dense film or a film with less $SiO_2$ incorporated from the substrate.

The XPS analysis of composition for the TDEAHf and for the TDMAHf demonstrated that all process conditions had negligible carbon incorporation (<1%). For the TDEAHf, there seems to be an increase in oxygen to Hf ratio at higher pressures, 8 Torr, and intermediate temperatures, 500° C. For the TDMAHf, there was less change in stoichiometry with condition, with highest oxygen concentrations at 400° C. From past experience, the highest oxygen content films have had the lowest leakage for a particular capacitance.

TEM was used to examine the interface of a nominal 50 Å film grown from each of the precursors at 400° C. Film G161 was grown at 400° C., 8 Torr from TDMAHf with a growth time of 43 seconds; Film G163 was grown at 400° C., 0.8 Torr from TDEAHf with a growth time of 60 seconds. TEM showed the interfaces of both films with underlying Si to be clean of any interfacial silicon oxide. In addition, it is clearly shown that the films are crystalline. It is expected that mixing Si oxide with the Hf oxide in the growth process would yield an amorphous film.

Process and Chemistry for Deposition of Hafnium Silicate films from Alkylamido Precursors One of the issues in growing a gate dielectric by a CVD process is minimizing the growth of interfacial $SiO_2$. There is some evidence that interfacial $SiO_2$ will grow even if the only oxygen present in the process is in an oxygen-containing precursor, such as an alcoxide or a mixed alcoxide-β-diketonate. The experiment discussed hereinabove demonstrated the viability of two hafnia precursors specifically, $Hf(NMe_2)_4$ and $Hf(Net_2)_4$ hereafter referred to as TDMAHf and TDEAHf, respectively. This experiment examines the viability of the corresponding silicon precursors: $Si(NMe_2)_3Cl$ and $Si(NEt_2)_2Cl_2$. The silica precursors are examined using the same process conditions.

The growth rates of both precursors are too low for a viable silica process in $N_2O$ over the temperature and pressure range examined (0.8 to 8 Torr, 400–600° C.). This is not surprising based on the growth rates of precursors such as bis(tertiarybutylamino) silane $H_2Si(N-tBu)_2$ (i.e., U.S. Pat. No. 5,976,991) at temperatures below 600° C. What is unexpected is that although growth rates for $SiO_2$ from $Si(NMe_2)_3Cl$ and $Si(NEt_2)_2Cl_2$ is slow in a $N_2O$ atmosphere, the presence of Hf enhances the decomposition of $Si(NEt_2)_2Cl_2$ to create a mixed Hf—Si—O film at manufacturable growth rates. Additionally, oxygen ambients at temperatures below 500° C. might be viable with the hafnium precursors.

Experimental

Figure 7A:
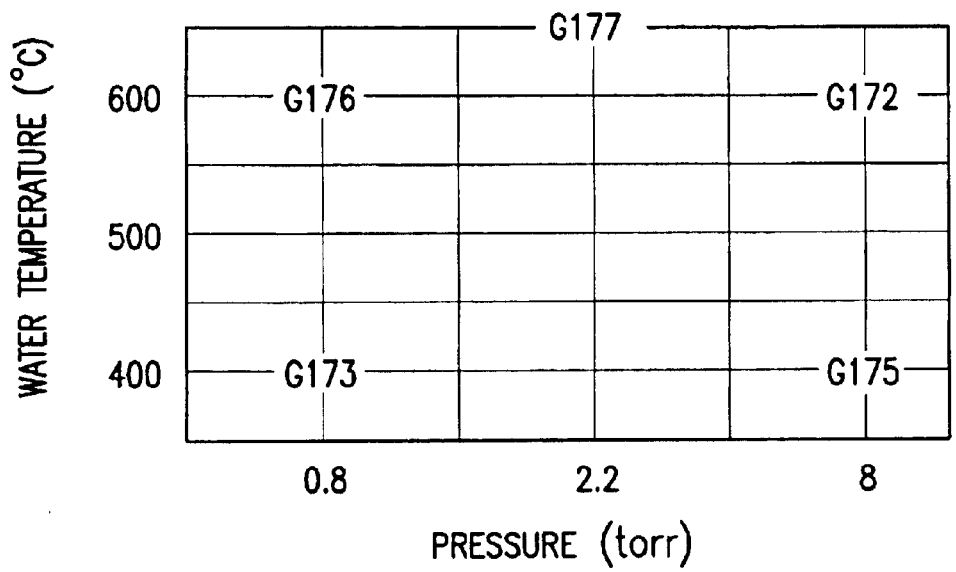
FIGS. 7A and 7B show a limited pressure-temperature matrix for $Si(N(C_2H_5)_2)_2Cl_2$ (Bis(diethyl-amino)dichlorosilane) and $Si(N(CH_3)_2)_3Cl$ (Tris(dimethyl-amino)chlorosilane in $N_2O$.
Figure 7B:
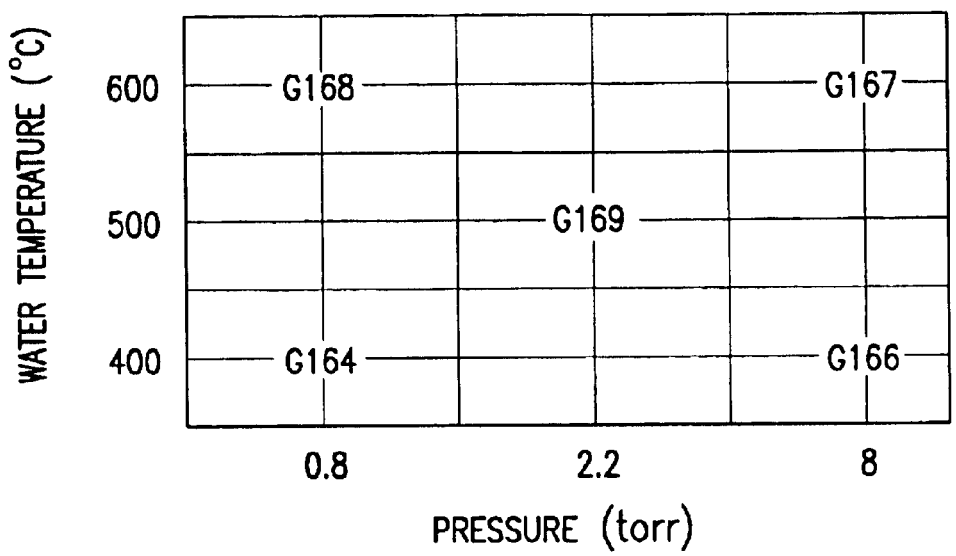

Silica films were grown with the silicon precursors listed in Table III, $Si(NMe_2)_3Cl$ and $Si(NEt_2)_2Cl_2$. Precursor solutions were prepared at 0.1M Si in octane. Substrates of (100) Si were prepared with an SC1 treatment followed by dilute HF to remove any native $SiO_2$. The generic process conditions for the experiments are shown in Table IV. Results from the growth of hafnia films encouraged us to center these initial experiments on growth in an $N_2O$ atmosphere although growth in $O_2$ or other oxidizer could be used at temperatures at or below 500° C. A limited pressure-temperature matrix was performed for each Si precursor using the $N_2O$ ambient as shown in FIGS. 7A and 7B.

TABLE III

Precursors used for film deposition.

| | | |
|---|---|---|
| (Bis(diethyl-amino)dichlorosilane) | $Si(N(C_2H_5)_2)_2Cl_2$ | |
| (Tris(dimethyl-amino)chlorosilane) | $Si(N(CH_3)_2)_3Cl$ | |
| Tetrakis(diethyl-amino)hafnium | $Hf(N(C_2H_5)_2)_4$ | TDEAHf |
| Tetrakis(dimethyl-amino)hafnium | $Hf(N(CH_3)_2)_4$ | TDMAHf |

TABLE IV

Generic process conditions

| | |
|---|---|
| Precursor solution | 0.10 M in octane |
| Precursor solution delivery rate | 0.10 ml/min |
| Vaporization Temperature | 150° C. |

TABLE IV-continued

Generic process conditions

| | |
|---|---|
| Run time | 10 minutes |
| Carrier gas | 100 sccm Ar |
| Heating and Cooling process gas | 500 sccm Ar |
| Run time process gas | 400 sccm N$_2$O |
| Pressure | 0.8, 2.2, or 8.0 Torr |
| Temperature | 400–650° C. wafer surface |

From NMR studies of precursor compatibility, it was shown that Si(NEt$_2$)$_2$Cl$_2$ is compatible with TDEAHf in solution, with any ligand exchange being degenerate. Si(NMe$_2$)$_3$Cl is compatible with both TDEAHf and TDMAHf. A solution of 0.05M TDEAHf:0.05M Si(NEt$_2$)$_2$Cl$_2$ was produced by mixing the two 0.1M solutions. This mixture was used to grow films over the entire matrix of process conditions.

Film thickness was measured using single-wavelength ellipsometry at 70° incidence angle, and XRF. For SiO$_2$ deposition, all films were less than 30 Å thick, so an index of refraction could not be measured accurately. Film thickness was assigned based on an assumed index of refraction, n=1.46, typical of high quality thermal oxide. For HfO$_2$, the XRF was calibrated by assuming the X-ray efficiencies were equivalent to TaO$_{2.5}$, for which standards that been measured by RBS. The Hf:Si composition was estimated by assuming that both are fully oxidized and fully dense. The ellipsometric thickness not accounted for by HfO$_2$ was assigned to SiO$_2$, and composition was calculated from these two thicknesses.

Results

Figure 8:
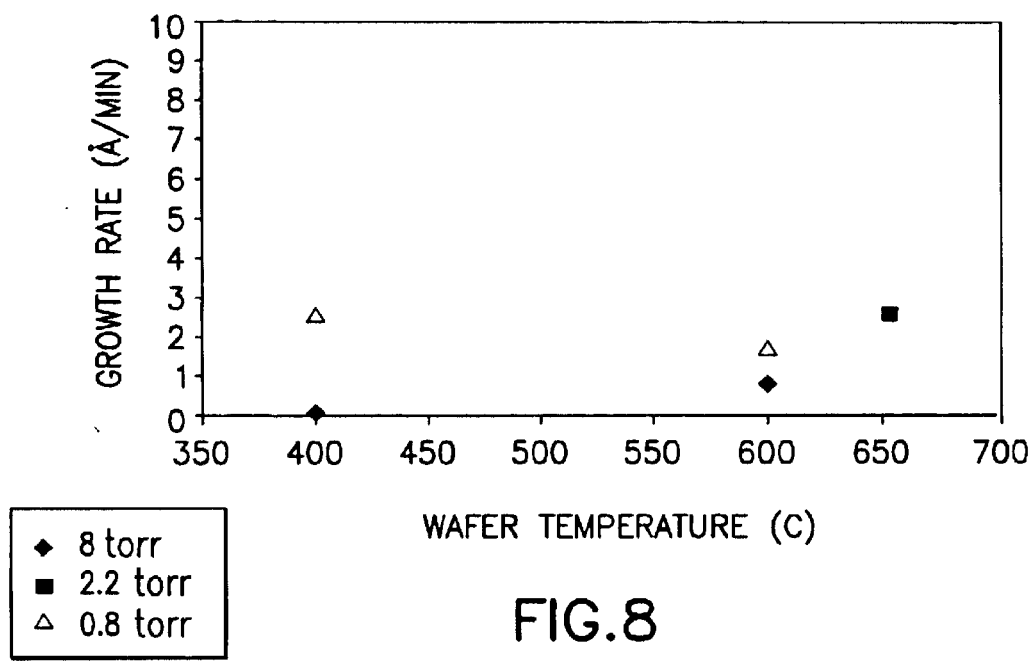
FIG. 8 shows the growth rate of silica from $Si(N(C_2H_5)_2)_2Cl_2$ (Bis(diethyl-amino)dichlorosilane) in $N_2O$ ambient.
Figure 9:
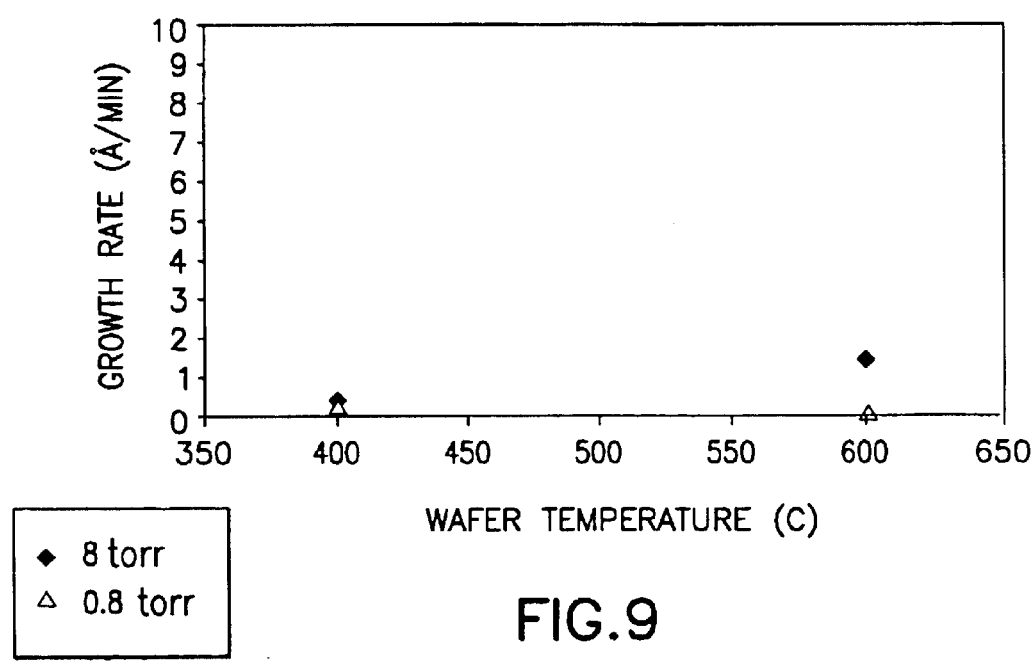
FIG. 9 shows the growth rate of silica from $Si(N(CH_3)_2)_3Cl$ (Tris(dimethyl-amino)chlorosilane in $N_2O$ ambient.

Growth rates of SiO$_2$ were less than 3 Å/min under all conditions as shown in FIG. 8 and FIG. 9. There is some indication that the Si(NEt$_2$)$_2$Cl$_2$ may form silica films a little bit more readily, however, none of the growth rates are sufficient for the two precursors under the instant conditions.

Figure 10:
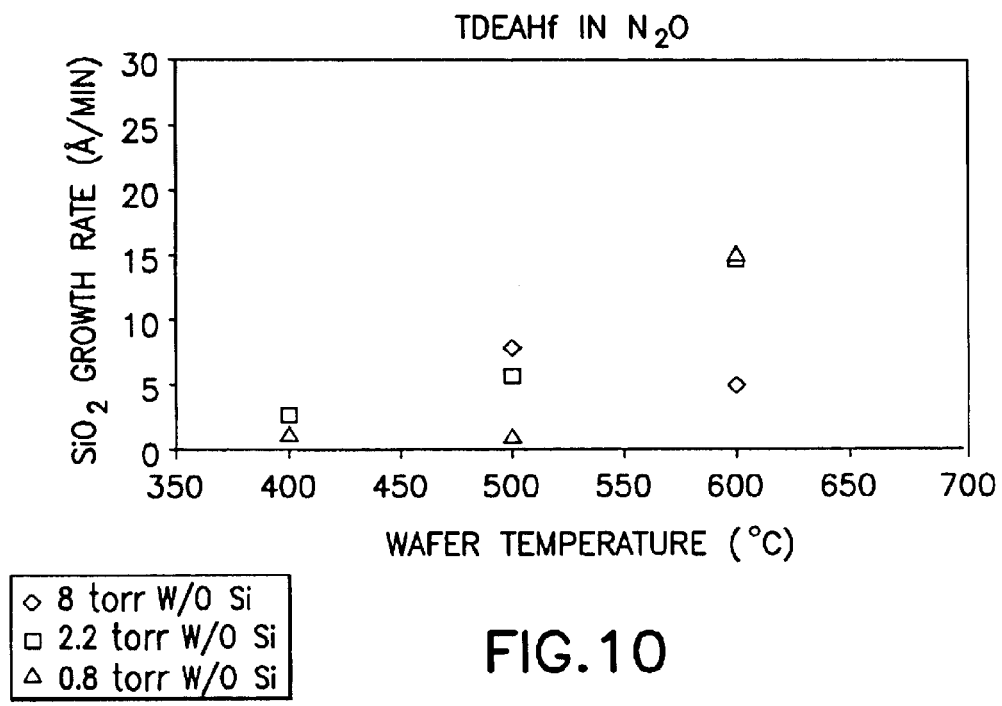
FIG. 10 shows the growth rate of $SiO_2$ under a $HfO_2$ film with no silicon precursor present.
Figure 11:
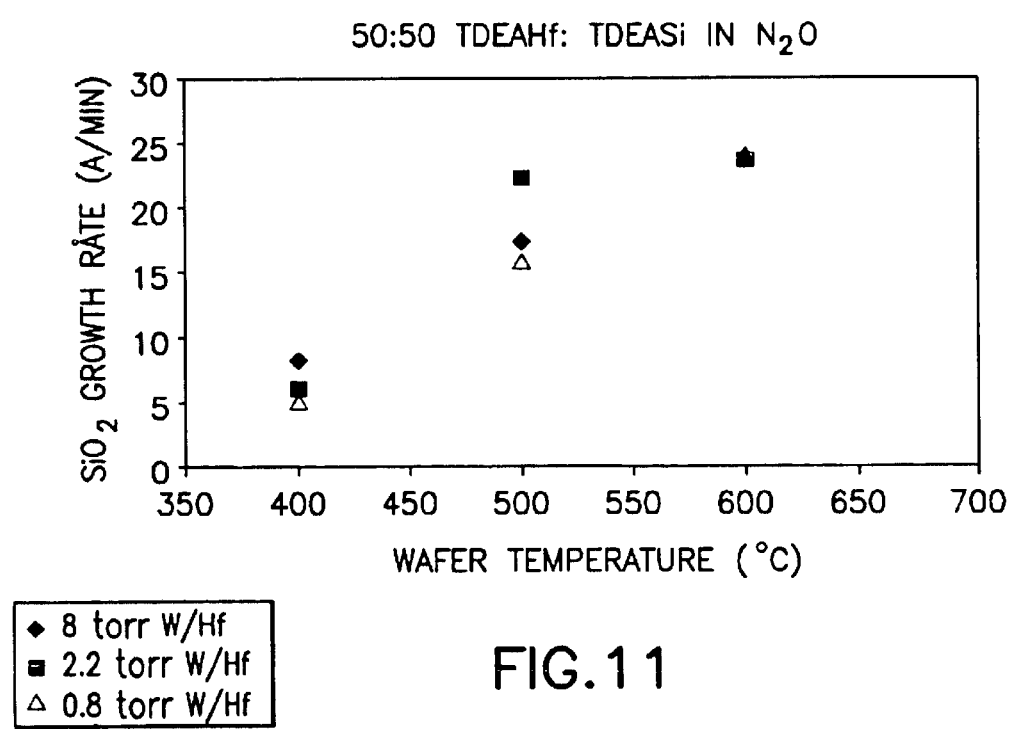
FIG. 11 shows the growth rate of $SiO_2$ from $Si(N(C_2H_5)_2)_2Cl_2$ (Bis(diethyl-amino)dichlorosilane when co-deposited with $HfO_2$ from $Hf(N(C_2H_5)_2)_4$ (Tetrakis(diethyl-amino)hafnium in $N_2O$ ambient.

The growth of SiO$_2$ with only the TDEAHf, as measured by the subtraction of ellipsometric thickness from XRF thickness (shown in FIG. 10) was greater than that from the Si(NEt$_2$)$_2$Cl$_2$ precursor alone (FIG. 8) Films grown from the precursor mixture (TDEAHf+Si(NEt$_2$)$_2$Cl$_2$) showed still higher SiO$_2$ growth rates as shown in FIG. 11. This increased growth rate compared to FIG. 8 is unexpected and should be quite useful for the growth of hafnium silicate films of uniform Hf:Si composition through the thickness of the film.

The films have a mixed Si:Hf composition on the film surface. The constant SiO$_2$ growth rate over the range of 500–600° C. at 2.2 Torr being the same as 0.8 Torr at 600° C. is taken as evidence of mass transport limited deposition over the range of the process. The addition of water vapor or O$_2$, should further decrease the temperature window wherein both Hf and Si alkylamido precursors transport and decompose reliably.

What is claimed is:

1. A CVD precursor composition for forming a thin film dielectric on a substrate, such precursor composition including a vapor source reagent-mixture including a metalloamide source reagent compound selected from the group consisting of:

M(NR$^1$R$^2$)$_x$; and

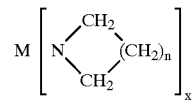

wherein M is selected from the group consisting of Zr, Hf, Y, La, Lanthanide series elements, Ta, Ti, Al; N is nitrogen; each of R$^1$ and R$^2$ is same or different and is independently selected from the group consisting of H, aryl, perfluoroaryl, C$_1$–C$_8$ alkyl, C$_1$–C$_8$ perfluoroalkyl, alkylsilyl; and x is the oxidation state on metal M; and it is from 1–6; and an aminosilane source reagent compound selected from the group consisting of:

H$_x$SiA$_y$(NR$^1$R$^2$)$_{4-x-y}$; and

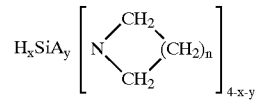

wherein H is hydrogen; x is from 0 to 3; Si is silicon; A is a halogen; Y is from 0 to 3; N is nitrogen; each of R$^1$ and R$^2$ is same or different and is independently selected from the group consisting of H, aryl, perfluoroaryl, C$_1$–C$_8$ alkyl, and C$_1$–C$_8$ perfluoroalkyl; and n is from 1–6; x is from 0 to 3; Si is silicon; A is a halogen; Y is from 0 to 3; N is nitrogen; n is from 1–6.

2. The CVD precursor composition according to claim 1, wherein the aminosilane soiree reagent compound is selected from the group consisting of: Si(NMe$_2$)$_3$Cl, Si(NEt$_2$)$_2$Cl$_2$, Si(NMe$_2$)$_4$, and Si(NEt$_2$)$_4$.

3. The CVD precursor composition according to claim 1, wherein the metalloamide source reagent compound and the aminosilane source reagent compound are injected by liquid delivery into a chemical vapor deposition chamber.

4. The CVD precursor composition according to claim 1, wherein the metalloamide source reagent compound and the aminosilane source reagent compound are delivered by bubbler into a chemical vapor deposition chamber.

5. The CVD precursor composition according to claim 1, wherein the precursor composition further comprises a solvent medium selected from the coup consisting of: ethers, glymes, tetraglymes, amines, polyamines, alcohols, glycols, aliphatic hydrocarbon solvents, aromatic hydrocarbon solvents, cyclic ethers and combinations of two or more of the foregoing.

6. The CVD precursor composition according to claim 1, wherein the metalloamide source reagent compound is injected by liquid delivery into a chemical vapor deposition chamber.

7. A CVD precursor composition for forming a thin film dielectric on a substrate, such precursor composition including at least one aminosilane source reagent compound selected from the group consisting of:

H$_x$SiA$_y$(NR$^1$R$^2$)$_{4-x-y}$; and

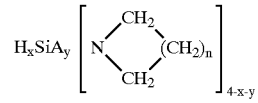

wherein H is hydrogen; x is from 0 to 3; Si is silicon; A is a halogen; Y is from 1 to 3; N is nitrogen; each of R$^1$ and R$^2$ is same or different and is independently selected from the group consisting of H, aryl, perfluoroaryl, $C_1$–$C_8$ alkyl, and $C_1$–$C_8$ perfluoroalkyl; and n is from 1–6.

8. A CVD precursor composition for forming a thin film dielectric on a substrate, such precursor composition including at least one aminosilane source reagent compound selected from the group consisting of $Si(NMe_2)_2Cl$, $Si(NEt_2)_2Cl_2$, $Si(NMe_2)_4$, and $Si(NEt_2)_4$.

9. The CVD precursor composition according to claim 7, wherein $R^1$ and $R^2$ of the aminosilane are methyl.

10. The CVD precursor composition according to claim 7, wherein $R^1$ and $R^2$ ethyl.

11. A CVD precursor composition for forming a thin film dielectric on a substrate, such precursor composition including at least one aminosilane source reagent compound having the formula:

$$H_xSiA_y(NR^1R^2)_{4-r-yt}$$

wherein H is hydrogen; x is from 0 to 3; Si is silicon; A is halogen; Y is from 0 to 3; N is nitrogen; $R^1$ is methyl, $R^2$ is ethyl; and n is from 1–6.

12. The CVD precursor composition according to claim 11, wherein the aminosilane source reagent compound is $Si(NMeEt)_4$.

13. A CVD precursor composition for forming a thin film dielectric on a substrate, such precursor composition including at least one aminosilane source reagent compound selected from the group consisting of:

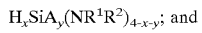

$$H_xSiA_y(NR^1R^2)_{4-x-y}; \text{ and}$$

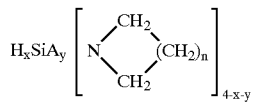

wherein H is hydrogen; x is from 0 to 3; Si is silicon; A is a halogen; Y is from 0 to 3; N is nitrogen; each of $R^1$ and $R^2$ is same or different and is independently selected from the group consisting of H, aryl, perfluoroaryl, $C_1$–$C_8$ alkyl, and $C_1$–$C_8$ perfluoroalkyl; and n is from 1–6 and a solvent medium selected from the group consisting of: ethers, glymes, tetraglymes, amines, polyamines, alcohols, glycols, aliphatic hydrocarbon solvents, aromatic hydrocarbon solvents, cyclic ethers and combinations of two or more of the foregoing.

14. The CVD precursor composition according to claim 13, wherein the solvent is octane.

15. The CVD precursor composition according to claim 13, wherein the aminosilane source reagent compound is injected by liquid delivery into a chemical vapor deposition chamber.

16. The CVD precursor of claim 13, wherein the precursor composition further comprises a metalloamide source reagent compound selected from the group consisting of:

$$M(NR^1R^2)_x; \text{ and}$$

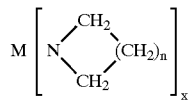

wherein M is selected from the group consisting of: Zr, Hf, Y, La, Lanthanide series elements, Ta, Ti, Al; N is nitrogen each of $R^1$ and $R^2$ is same or different and is independently selected from the group consisting of H, aryl, perfluoroaryl, $C_1$–$C_8$ alkyl, $C_1$–$C_8$ perfluoroalkyl, alkylsilyl; and x is the oxidation state on metal M; end n is from 1–6.

17. The CVD precursor composition according to claim 16, wherein $R^1$ and $R^2$ of the metalloamide source reagent are methyl.

18. The CVD precursor composition according to claim 16, wherein $R^1$ and $R^2$ of the metalloamide source reagent compound are ethyl.

19. The CVD precursor composition according to claim 16, wherein $R^1$ of the metalloamide source reagent compound is methyl and $R^2$ of the metalloamide source reagent compound is ethyl.

20. The CVD precursor composition according to claim 16, wherein M is Zr.

21. The CVD precursor composition according to claim 16, wherein M is Hf.

22. The CVD precursor composition according to claim 16, wherein the metalloamide source reagent compound is selected from the group consisting of: $Zr(NMe_2)_4$, $Zr(NMeEt)_4$, $Zr(NEt_2)_4$, $Ta(NEt_2)_5$, $Ta(NMeEt_2)_5$, $Ta(NMeEt)_5$, $Zr(NiPr_2)_4$, $Zr(NMe_2)_2(NPr_2)_2$, $Zr(NC_6H_{12})_4$, $Zr(NEt_2)_2(NPr_2)_2$, $Hf(NEt_2)_4$, $Hf(NMe_2)_4$, $Hf(NMeEt)_4$, $La(NMe_2)_3$, $La(NEt_2)_3$, $La(NMeEt)_3$, $Al(NMe_2)_3$, $Al(NEt_2)_3$, $Y(NMe_2)_3$, $Y(NEt_2)_3$, $Y(NMeEt)_3$, $Ti(NMe_2)_4$, $Ti(NEt_3)_4$, $Ti(NMeEt)_4$, $Ta(NMe_2)_5$, $Ta(NEt_2)_5$.

23. The CVD precursor composition according to claim 16, wherein the metalloamide source reagent compound is selected from the group consisting of $Zr(NMe_2)_4$, $Zr(NEt_2)_4$, $Zr(NMeEt)_4$, $Hf(NEt_2)_4$, $Hf(NMe_2)_4$, and $Hf(NMeEt)_4$.

24. A CVD multi-component, single source reagent composition useful for forming a silicate thin film dielectric on a substrate, the source reagent composition comprising at least one metalloamide vapor source reagent compound selected from the group consisting of:

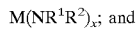

$$M(NR^1R^2)_x; \text{ and}$$

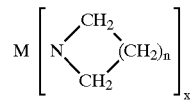

wherein M is selected from the group consisting of: Zr, Hf, Y, La, Lanthanide series elements, Ta, Ti, Al; N is nitrogen; each of $R^1$ and $R^2$ is same or different and is independently selected from the group consisting of H, aryl, perfluoroaryl, $C_1$–$C_8$ alkyl, $C_1$–$C_8$ perfluoroalkyl, alkylsilyl; and x is the oxidation state on metal M; and n is from 1–6; and an aminosilane vapor source reagent compound selected from the group consisting of:

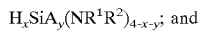

$$H_xSiA_y(NR^1R^2)_{4-x-y}; \text{ and}$$

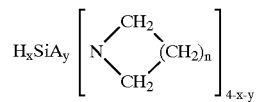

wherein H is hydrogen; x is from 0 to 3; Si is silicon; A is a halogen; Y is from 0 to 3; N is nitrogen; each of $R^1$ and $R^2$ is same or different and is independently selected from the group consisting of H, aryl, perfluoroaryl, $C_1$–$C_8$ alkyl, and $C_1$–$C_8$ perfluoroalkyl; and a is from 1–6; and a solvent medium in which the metalloamide compound and the aminosilane compound are soluble or suspendable.

25. A CVD method of forming a dielectric thin film on a substrate, comprising the steps of:
vaporizing a source reagent composition comprising at least one metalloamide source reagent compound and at least one aminosilane source reagent compound, to form a source reagent precursor vapor;
transporting the source reagent precursor vapor into a chemical vapor deposition zone, optionally using a carrier gas;
contacting the source reagent precursor vapor with a substrate in said chemical vapor deposition zone at elevated temperature to deposit a dielectric thin film on the substrate.

26. The method according to claim 25, wherein the metalloamide source reagent compound is selected from the group consisting of:

$M(NR^1R^2)_x$; and

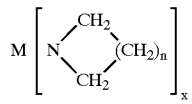

wherein M is selected from the group consisting of Zr, Hf, Y, La, Lanthanide series elements, Ta, Ti, Al; N is nitrogen; each of $R^1$ and $R^2$ is same or different and is independently selected from the group consisting of H, aryl, perfluoroaryl, $C_1$–$C_8$ alkyl, $C_1$–$C_8$ perfluoroalkyl, alkylsilyl; and x is the oxidation state on metal M; and n is from 1–6.

27. The CVD method according to claim 25, wherein the source reagent composition is vaporized in a liquid delivery apparatus.

28. The CVD method according to claim 25, wherein the source reagent vapor is transported into the chemical vapor deposition chamber in a pulsed deposition mode.

29. The CVD method according to claim 25, wherein the dielectric thin film is deposited in the absence of an oxidizer.

30. The CVD method according to claim 25, wherein the source reagent vapor further comprises a co-reactive gas.

31. The CVD method according to claim 30, wherein the co-reactive gas is selected from the group consisting of ozone, water vapor and reactive alcohols.

32. The CVD method according to claim 25, wherein the metalloamide source reagent compound is selected from the group consisting of: $Zr(NMe_2)_4$, $Zr(NEt_2)_4$, $Zr(NMeEt)_4$, $Hf(NMe_2)_4$, $Hf(NEt_2)_4$, and $Hf(NMeEt)_4$.

33. The CVD method according to claim 25, wherein the metalloamide source reagent compound is $Hf(NMe_2)_4$.

34. A CVD method of forming a dielectric thin film on a substrate, comprising the steps of:
vaporizing a source reagent composition comprising at least one metalloamide precursor dissolved or suspended in octane, to form a source reagent precursor vapor;
transforming the source reagent precursor vapor into a chemical vapor deposition zone, optionally using a carrier gas;
contacting the source reagent precursor vapor with a substrate in the chemical vapor deposition zone at elevated temperature, to deposit a dielectric thin film on the substrate.

35. The CVD method according to claim 25, wherein the metalloamide source reagent compound is solubilized or suspended in a solvent.

36. The CVD method according to claim 25, wherein the metalloamide source reagent compound is $Zr(NMe_2)_4$.

37. A method of forming a dielectric thin film a substrate, comprising the steps of:
vaporizing a source reagent composition comprising $La(NMe_2)$ and $Zr(NMe_2)_4$ to form a source reagent precursor vapor;
transporting the source reagent precursor vapor into a chemical vapor deposition zone, optionally using a carrier gas;
contacting the source reagent precursor vapor with a substrate in the chemical vapor deposition zone at elevated temperature to deposit a dielectric thin film on the substrate.

38. A CVD method of forming a dielectric thin film on a substrate, comprising the steps of:
vaporizing a source reagent composition comprising a $X(NMe_2)_3$, to form a source reagent precursor vapor;
transporting the source reagent precursor vapor into a chemical vapor deposition zone, optionally using a carrier gas;
contacting the source reagent precursor vapor with a substrate in said chemical vapor deposition zone at elevated temperature to deposit a dielectric thin film on the substrate.

39. A CVD method of forming a dielectric thin film on a substrate, comprising the steps of:
vaporizing a source reagent composition comprising $Hf(N(CH_3)_2)_4$ and $La(N(CH_3)_2)_3$, to form a source reagent precursor vapor;
transporting the source reagent precursor vapor into a chemical vapor deposition zone, optionally using a carrier gas;
contacting the source reagent precursor vapor with a substrate in the chemical vapor deposition zone at elevated temperature to deposit a dielectric thin film on the substrate.

40. The CVD method according to claim 25, wherein the metalloamide source reagent compound is $Hf(NMe_2)_4$ and the aminosilane source reagent compound is $Si(NMe_2)_3Cl$.

41. The CVD method according to claim 25, wherein the carrier gas is selected from the group consisting of: He, Ar, $H_2$, $N_2$ and $O_2$.

42. The CVD method according to claim 25, further comprising an oxidizing gas selected from the group consisting of: $O_2$, $N_2O$, NO and $O_3$.

43. The CVD method according to claim 42, wherein the oxidizing gas is $N_2O$.

44. The CVD method according to claim 25, further comprising an oxidizing gas, wherein the oxidizing gas is $N_2O$.

45. The CVD method according to claim 25, wherein the metalloamide source reagent compound is vaporized at a temperature in a range of from about 100° C. to about 300° C.

46. The CVD method according to claim 25, wherein the temperature in the chemical vapor deposition zone is between about 350° C. to about 750° C.

* * * * *

UNITED STATES PATENT AND TRADEMARK OFFICE
CERTIFICATE OF CORRECTION

PATENT NO. : 6,869,638 B2
APPLICATION NO. : 09/954831
DATED : March 22, 2005
INVENTOR(S) : Thomas H. Baum It is certified that error appears in the above-identified patent and that said Letters Patent is hereby corrected as shown below:

Column 22, line 12: "and it is from 1-6" should be --and n is from 1-6--

Column 22, lines 23-29:
"wherein H is hydrogen; x is from 0 to 3; Si is silicon; A is a halogen; Y is from 0 to 3; N is nitrogen; each of $R^1$ and $R^2$ is same or different and is independently selected from the group consisting of H, aryl, perfluoroaryl, $C_1$-$C_8$ alkyl, and $C_1$-$C_8$ perfluoroalkyl; and n is from 1-6; x is from 0 to 3; Si is silicon; A is a halogen; Y is from 0 to 3; N is nitrogen; n is from 1-6."

should be

--wherein H is hydrogen; x is from 0 to 3; Si is silicon; A is a halogen; y is from 0 to 3; N is nitrogen; each of $R^1$ and $R^2$ is same or different and is independently selected from the group consisting of H, aryl, perfluoroaryl, $C_1$-$C_8$ alkyl, and $C_1$-$C_8$ perfluoroalkyl; and n is from 1-6.--

Column 22, line 31: "aminosilane soiree reagent compound" should be --aminosilane source reagent compound--

Column 22, line 44: "selected from the coup consisting of" should be --selected from the group consisting of--

Column 22, line 65 to column 23, line 2:

"wherein H is hydrogen; x is from 0 to 3; Si is silicon; A is a halogen; Y is from 1 to 3; N is nitrogen; each of $R^1$ and $R^2$ is same or different and is independently selected from the group consisting of H, aryl, perfluoroaryl, $C_1$-$C_8$ alkyl, and $C_1$-$C_8$ perfluoroalkyl; and n is from 1 -6."

should be

Signed and Sealed this
Twenty-sixth Day of March, 2013

Teresa Stanek Rea
*Acting Director of the United States Patent and Trademark Office*

CERTIFICATE OF CORRECTION (continued)

U.S. Pat. No. 6,869,638 B2

--wherein H is hydrogen; x is from 0 to 3; Si is silicon; A is a halogen; y is from 1 to 3; N is nitrogen; each of $R^1$ and $R^2$ is same or different and is independently selected from the group consisting of H, aryl, perfluoroaryl, $C_1$-$C_8$ alkyl, and $C_1$-$C_8$ perfluoroalkyl; and n is from 1-6.--

Column 23, line 6: "$Si(NMe_2)_2Cl$" should be --$Si(NMe_2)_3Cl$--

Column 23, line 11: "$R^1$ and $R^2$ ethyl" should be --$R^1$ and $R^2$ are ethyl--

Column 23, line 17: "$H_xSiA_y(NR^1R^2)_{4-r-yt}$" should be --$H_xSiA_y(NR^1R^2)_{4-x-y}$--

Column 23, lines 19-21:

"wherein H is hydrogen; x is from 0 to 3; Si is silicon; A is halogen; Y is from 0 to 3; N is nitrogen; $R^1$ is methyl, $R^2$ is ethyl; and n is from 1-6."

should be

--wherein H is hydrogen; x is from 0 to 3; Si is silicon; A is a halogen; y is from 0 to 3; N is nitrogen; $R^1$ is methyl; and $R^2$ is ethyl.--

Column 23, line 38: "Y is from 0 to 3" should be --y is from 0 to 3--

Column 24, line 2: "end n is from 1-6." should be --and n is from 1-6.--

Column 24, line 20: "$Ta(NMeEt_2)_5$" should be --$Ta(NMe_2)_5$--

Column 24, line 25: "$Ti(NEt_3)_4$" should be --$Ta(NEt_2)_4$--

Column 24, line 61: "Y is from 0 to 3" should be --y is from 0 to 3--

Column 24, line 64: "and a is from 1-6" should be --and n is from 1-6--

Column 25, line 55: "transforming" should be --transporting--

Column 26, line 3: "dielectric thin film a substrate" should be --dielectric thin film on a substrate--

Column 26, line 6: "$La(NMe_2)$" should be --$La(NMe_2)_3$--

Column 26, line 17-18: "$_a X(NMe_2)_3$" should be --$Y(NMe_2)_3$--